United States Patent
Iwasaki

(10) Patent No.: US 9,512,177 B2
(45) Date of Patent: Dec. 6, 2016

(54) METHOD FOR PRODUCING γ-GLUTAMYL-VALYL-GLYCINE CRYSTAL

(71) Applicant: AJINOMOTO CO., INC., Tokyo (JP)

(72) Inventor: Eriko Iwasaki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 11 days.

(21) Appl. No.: 14/618,561

(22) Filed: Feb. 10, 2015

(65) Prior Publication Data

US 2015/0361133 A1  Dec. 17, 2015

Related U.S. Application Data

(63) Continuation of application No. PCT/JP2013/071686, filed on Aug. 9, 2013.

(30) Foreign Application Priority Data

Aug. 10, 2012  (JP) ................................. 2012-178350

(51) Int. Cl.
| | |
|---|---|
| *C07K 5/08* | (2006.01) |
| *C12P 21/02* | (2006.01) |
| *C07K 5/02* | (2006.01) |
| *C07K 5/093* | (2006.01) |
| *C07K 1/30* | (2006.01) |

(52) U.S. Cl.
CPC ........... *C07K 5/0819* (2013.01); *C07K 5/0215* (2013.01); *C12P 21/02* (2013.01); *C07K 1/306* (2013.01)

(58) Field of Classification Search
None
See application file for complete search history.

(56) References Cited

U.S. PATENT DOCUMENTS

| | | | |
|---|---|---|---|
| 7,288,389 B2 | 10/2007 | Hara et al. | |
| 7,306,933 B2 | 12/2007 | Dien et al. | |
| 7,531,340 B2 | 5/2009 | Hara et al. | |
| 7,736,871 B2 | 6/2010 | Hara et al. | |
| 7,736,876 B2 | 6/2010 | Hara et al. | |
| 7,809,511 B2 | 10/2010 | Van Dien et al. | |
| 8,030,036 B2 | 10/2011 | Van Dien et al. | |
| 8,039,232 B2 | 10/2011 | Hara et al. | |
| 8,173,605 B2 | 5/2012 | Ohsu et al. | |
| 8,329,428 B2 | 12/2012 | Hara et al. | |
| 8,389,241 B2 | 3/2013 | Hara et al. | |
| 8,420,144 B2 | 4/2013 | Eto et al. | |
| 8,753,841 B2 | 6/2014 | Hara et al. | |
| 2004/0204577 A1 | 10/2004 | Hara et al. | |
| 2009/0246835 A1 | 10/2009 | Iwatani et al. | |
| 2011/0097805 A1 | 4/2011 | Ohsu et al. | |

FOREIGN PATENT DOCUMENTS

| | | |
|---|---|---|
| JP | 2-231085 A | 9/1990 |
| JP | 2012-085637 A | 5/2012 |
| WO | WO 2004/011653 A1 | 2/2004 |
| WO | WO 2005/010175 A1 | 2/2005 |
| WO | WO2007/055393 A1 | 5/2007 |
| WO | WO 2012/108408 A1 | 8/2012 |

OTHER PUBLICATIONS

Written Opinion (PCT/ISA/237) issued Sep. 25, 2013 in corresponding PCT/JP2013/071686.
International Search Report issued Sep. 25, 2013 in corresponding PCT/JP2013/071686.
Journal ofthe American Chemical Society (1958), 80, pp. 1154-1158.
Proc. Natl. Acad. Sci. USA, vol. 97, No. 12, pp. 6640-6645, 2000.
J. Bacteriol., 184 (18): 5200-3, Sep. 2002.
J. Bacteriol. 168(3): 1325-1331, Dec. 1986.
Recent Highlights in Flavor Chemistry & Biology, 2008, p. 227-232.
Biochem Biophys Res Commun., 1988, vol. 150, p. 33-38.
Amino Acids, 2007, vol. 32, p. 333-340.
Extended European Search Report issued Apr. 19, 2016 in Patent Application No. 13828622.4.

*Primary Examiner* — Suzanne M Noakes
(74) *Attorney, Agent, or Firm* — Oblon, McClelland, Maier & Neustadt, L.L.P.

(57) ABSTRACT

The present invention provides a method for efficiently producing a γ-glutamyl-valyl-glycine crystal. Specifically, the present invention provides a method for producing a γ-glutamyl-valyl-glycine crystal, which includes the steps of: preparing a mixed solution of valyl-glycine or a salt thereof and γ-glutamyl-valyl-glycine, wherein the mixed solution contains valyl-glycine or the salt thereof in an amount of 20 mass % or more relative to the mass of γ-glutamyl-valyl-glycine; adjusting the amount of valyl-glycine or the salt thereof in the prepared mixed solution to 0.1 mass % or more and less than 20 mass % relative to the mass of γ-glutamyl-valyl-glycine to prepare a γ-glutamyl-valyl-glycine solution; and subjecting the γ-glutamyl-valyl-glycine solution to a crystallization procedure to produce the γ-glutamyl-valyl-glycine crystal.

12 Claims, 4 Drawing Sheets

SEQUENCE LISTING

<160> NUMBER OF SEQ ID NOS: 14

<210> SEQ ID NO 1
<211> LENGTH: 1743
<212> TYPE: DNA
<213> ORGANISM: Escherichia coli

<220> FEATURE:
<221> NAME/KEY: CDS
<222> LOCATION: (1)..(1743)

<400> SEQUENCE: 1

| | | | | | | | | | | | | | | | | |
|---|---|---|---|---|---|---|---|---|---|---|---|---|---|---|---|---|
| atg | ata | aaa | ccg | acg | ttt | tta | cgc | cgg | gtg | gcc | att | gct | gct | ctg | ctc | 48 |
| Met | Ile | Lys | Pro | Thr | Phe | Leu | Arg | Arg | Val | Ala | Ile | Ala | Ala | Leu | Leu | |
| 1 | | | | 5 | | | | | 10 | | | | | 15 | | |
| tca | gga | agt | tgt | ttt | agc | gcc | gcc | gcc | gcg | cct | cct | gcg | ccg | ccc | gtc | 96 |
| Ser | Gly | Ser | Cys | Phe | Ser | Ala | Ala | Ala | Ala | Pro | Pro | Ala | Pro | Pro | Val | |
| | | | 20 | | | | | 25 | | | | | 30 | | | |
| tcg | tat | ggt | gtg | gag | gaa | gat | gtc | ttc | cac | ccg | gta | cgc | gcg | aaa | cag | 144 |
| Ser | Tyr | Gly | Val | Glu | Glu | Asp | Val | Phe | His | Pro | Val | Arg | Ala | Lys | Gln | |
| | | | | 35 | | | | | 40 | | | | | 45 | | |
| gga | atg | gta | gcg | tct | gtg | gac | gcc | act | gcc | act | cag | gtg | ggg | gtg | gat | 192 |
| Gly | Met | Val | Ala | Ser | Val | Asp | Ala | Thr | Ala | Thr | Gln | Val | Gly | Val | Asp | |
| | 50 | | | | | 55 | | | | | 60 | | | | | |
| att | ctc | aag | gag | ggc | ggg | aat | gcc | gtt | gat | gcc | gcc | gtg | gcg | gtg | ggc | 240 |
| Ile | Leu | Lys | Glu | Gly | Gly | Asn | Ala | Val | Asp | Ala | Ala | Val | Ala | Val | Gly | |
| 65 | | | | | 70 | | | | | 75 | | | | | 80 | |
| tac | gcg | ctg | gcg | gta | acg | cat | ccg | cag | gca | ggg | aat | ctg | ggc | ggt | ggt | 288 |
| Tyr | Ala | Leu | Ala | Val | Thr | His | Pro | Gln | Ala | Gly | Asn | Leu | Gly | Gly | Gly | |
| | | | | 85 | | | | | 90 | | | | | 95 | | |
| ggt | ttt | atg | tta | atc | cgc | tcg | aaa | aat | ggc | aat | acc | acg | gct | atc | gat | 336 |
| Gly | Phe | Met | Leu | Ile | Arg | Ser | Lys | Asn | Gly | Asn | Thr | Thr | Ala | Ile | Asp | |
| | | | 100 | | | | | 105 | | | | | 110 | | | |
| ttc | cgc | gaa | atg | gca | ccc | gcc | aaa | gcg | acc | cgc | gat | atg | ttc | ctc | gat | 384 |
| Phe | Arg | Glu | Met | Ala | Pro | Ala | Lys | Ala | Thr | Arg | Asp | Met | Phe | Leu | Asp | |
| | | | | 115 | | | | | 120 | | | | | 125 | | |
| gat | cag | ggc | aac | ccg | gac | agc | aaa | aaa | tca | ctc | act | tcg | cat | ctg | gct | 432 |
| Asp | Gln | Gly | Asn | Pro | Asp | Ser | Lys | Lys | Ser | Leu | Thr | Ser | His | Leu | Ala | |
| | 130 | | | | | 135 | | | | | 140 | | | | | |
| tcc | ggc | aca | ccg | ggt | acg | gta | gca | ggt | ttc | tcg | ctg | gcg | ctg | gat | aaa | 480 |
| Ser | Gly | Thr | Pro | Gly | Thr | Val | Ala | Gly | Phe | Ser | Leu | Ala | Leu | Asp | Lys | |
| 145 | | | | | 150 | | | | | 155 | | | | | 160 | |
| tac | ggc | acc | atg | ccg | ctg | aac | aaa | gtc | gtg | cag | ccc | gcg | ttt | aaa | ctg | 528 |
| Tyr | Gly | Thr | Met | Pro | Leu | Asn | Lys | Val | Val | Gln | Pro | Ala | Phe | Lys | Leu | |
| | | | | 165 | | | | | 170 | | | | | 175 | | |
| gca | cgc | gat | ggt | ttt | atc | gtt | aac | gac | gcg | ctg | gct | gac | gat | ctc | aaa | 576 |
| Ala | Arg | Asp | Gly | Phe | Ile | Val | Asn | Asp | Ala | Leu | Ala | Asp | Asp | Leu | Lys | |
| | | | 180 | | | | | 185 | | | | | 190 | | | |
| acc | tac | ggt | agc | gaa | gtg | ttg | ccg | aat | cac | gaa | aac | agt | aaa | gct | atc | 624 |
| Thr | Tyr | Gly | Ser | Glu | Val | Leu | Pro | Asn | His | Glu | Asn | Ser | Lys | Ala | Ile | |
| | | | | 195 | | | | | 200 | | | | | 205 | | |
| ttc | tgg | aaa | gag | ggc | gag | ccg | ctg | aaa | aag | ggc | gac | acg | ctg | gtg | cag | 672 |
| Phe | Trp | Lys | Glu | Gly | Glu | Pro | Leu | Lys | Lys | Gly | Asp | Thr | Leu | Val | Gln | |
| | 210 | | | | | 215 | | | | | 220 | | | | | |
| gcg | aac | ctg | gca | aag | agc | ctg | gag | atg | att | gct | gaa | aac | ggc | ccg | gac | 720 |
| Ala | Asn | Leu | Ala | Lys | Ser | Leu | Glu | Met | Ile | Ala | Glu | Asn | Gly | Pro | Asp | |
| 225 | | | | | 230 | | | | | 235 | | | | | 240 | |
| gaa | ttc | tat | aaa | ggc | acg | att | gcg | gaa | cag | atc | gcc | cag | gag | atg | cag | 768 |
| Glu | Phe | Tyr | Lys | Gly | Thr | Ile | Ala | Glu | Gln | Ile | Ala | Gln | Glu | Met | Gln | |
| | | | | 245 | | | | | 250 | | | | | 255 | | |
| aaa | aac | ggt | ggc | ttg | atc | act | aaa | gaa | gat | tta | gca | gcc | tat | aaa | gcg | 816 |
| Lys | Asn | Gly | Gly | Leu | Ile | Thr | Lys | Glu | Asp | Leu | Ala | Ala | Tyr | Lys | Ala | |
| | | | 260 | | | | | 265 | | | | | 270 | | | |
| gtc | gaa | cgc | act | ccg | ata | agc | ggc | gat | tat | cgc | ggg | tat | cag | gtt | tac | 864 |
| Val | Glu | Arg | Thr | Pro | Ile | Ser | Gly | Asp | Tyr | Arg | Gly | Tyr | Gln | Val | Tyr | |
| | | | | 275 | | | | | 280 | | | | | 285 | | |

```
                                                              -continued
tcc atg cca ccg cca tcc tcc ggc ggg atc cat atc gta caa atc ctc       912
Ser Met Pro Pro Pro Ser Ser Gly Gly Ile His Ile Val Gln Ile Leu
    290             295             300 aat att ctg gaa aac ttc gat atg aag aaa tac ggc ttt ggc agc gcc       960
Asn Ile Leu Glu Asn Phe Asp Met Lys Lys Tyr Gly Phe Gly Ser Ala
305             310             315             320 gat gcg atg caa atc atg gca gaa gcg gag aaa tac gcc tac gcc gac      1008
Asp Ala Met Gln Ile Met Ala Glu Ala Glu Lys Tyr Ala Tyr Ala Asp
                325             330             335 cgc tcg gaa tat ctt ggc gac ccg gat ttt gtc aaa gta ccg tgg cag      1056
Arg Ser Glu Tyr Leu Gly Asp Pro Asp Phe Val Lys Val Pro Trp Gln
            340             345             350 gcg ctg acc aat aaa gcc tat gcc aaa tct att gcc gat caa att gat      1104
Ala Leu Thr Asn Lys Ala Tyr Ala Lys Ser Ile Ala Asp Gln Ile Asp
        355             360             365 atc aat aaa gcg aag cca tcc agc gaa att cgc ccc ggc aag ctt gcg      1152
Ile Asn Lys Ala Lys Pro Ser Ser Glu Ile Arg Pro Gly Lys Leu Ala
    370             375             380 cct tat gag agt aat caa act acc cat tac tca gtg gtg gat aaa gat      1200
Pro Tyr Glu Ser Asn Gln Thr Thr His Tyr Ser Val Val Asp Lys Asp
385             390             395             400 ggt aac gcg gtg gcg gtg acc tat acg ctg aac acc acc ttc ggt acg      1248
Gly Asn Ala Val Ala Val Thr Tyr Thr Leu Asn Thr Thr Phe Gly Thr
                405             410             415 ggc att gtc gcg ggc gag agc ggt att ctg ctt aat aac cag atg gat      1296
Gly Ile Val Ala Gly Glu Ser Gly Ile Leu Leu Asn Asn Gln Met Asp
            420             425             430 gat ttc tcc gcc aaa ccg ggc gta ccg aac gtt tac ggg ctg gtg ggc      1344
Asp Phe Ser Ala Lys Pro Gly Val Pro Asn Val Tyr Gly Leu Val Gly
        435             440             445 ggt gat gcc aac gcc gtc ggg ccg aac aaa cgc ccg ctg tcg tcg atg      1392
Gly Asp Ala Asn Ala Val Gly Pro Asn Lys Arg Pro Leu Ser Ser Met
    450             455             460 tcg ccg acc att gtg gtg aaa gac ggt aaa acc tgg ctg gtt acc ggt      1440
Ser Pro Thr Ile Val Val Lys Asp Gly Lys Thr Trp Leu Val Thr Gly
465             470             475             480 agc cca ggc ggt agc cgg atc atc act aca gtg ctg caa atg gtg gtg      1488
Ser Pro Gly Gly Ser Arg Ile Ile Thr Thr Val Leu Gln Met Val Val
                485             490             495 aat agc atc gat tat ggc ttg aac gtc gcc gaa gcg acc aat gcg ccg      1536
Asn Ser Ile Asp Tyr Gly Leu Asn Val Ala Glu Ala Thr Asn Ala Pro
            500             505             510 cgt ttc cac cat cag tgg ttg ccg gac gag ctg cgt gtc gaa aaa ggg      1584
Arg Phe His His Gln Trp Leu Pro Asp Glu Leu Arg Val Glu Lys Gly
        515             520             525 ttt agc ccg gat acg ctc aag ctg ctg gaa gca aaa ggt cag aaa gtg      1632
Phe Ser Pro Asp Thr Leu Lys Leu Leu Glu Ala Lys Gly Gln Lys Val
    530             535             540 gcg ctg aaa gag gcg atg ggc agt aca caa agc att atg gtt ggg ccg      1680
Ala Leu Lys Glu Ala Met Gly Ser Thr Gln Ser Ile Met Val Gly Pro
545             550             555             560 gac ggt gag ttg tac ggc gca tcc gac ccg cgc tcg gtg gat gat tta      1728
Asp Gly Glu Leu Tyr Gly Ala Ser Asp Pro Arg Ser Val Asp Asp Leu
                565             570             575 acg gcg ggg tac taa                                                  1743
Thr Ala Gly Tyr
            580
```

```
<210> SEQ ID NO 2
<211> LENGTH: 580
<212> TYPE: PRT
<213> ORGANISM: Escherichia coli

<400> SEQUENCE: 2

Met Ile Lys Pro Thr Phe Leu Arg Arg Val Ala Ile Ala Ala Leu Leu
1               5                   10                  15

Ser Gly Ser Cys Phe Ser Ala Ala Ala Pro Ala Pro Pro Val
            20                  25                  30

Ser Tyr Gly Val Glu Glu Asp Val Phe His Pro Val Arg Ala Lys Gln
        35                  40                  45

Gly Met Val Ala Ser Val Asp Ala Thr Ala Thr Gln Val Gly Val Asp
    50                  55                  60

Ile Leu Lys Glu Gly Gly Asn Ala Val Asp Ala Ala Val Ala Val Gly
65                  70                  75                  80

Tyr Ala Leu Ala Val Thr His Pro Gln Ala Gly Asn Leu Gly Gly Gly
                85                  90                  95

Gly Phe Met Leu Ile Arg Ser Lys Asn Gly Asn Thr Thr Ala Ile Asp
            100                 105                 110

Phe Arg Glu Met Ala Pro Ala Lys Ala Thr Arg Asp Met Phe Leu Asp
        115                 120                 125

Asp Gln Gly Asn Pro Asp Ser Lys Lys Ser Leu Thr Ser His Leu Ala
    130                 135                 140

Ser Gly Thr Pro Gly Thr Val Ala Gly Phe Ser Leu Ala Leu Asp Lys
145                 150                 155                 160

Tyr Gly Thr Met Pro Leu Asn Lys Val Val Gln Pro Ala Phe Lys Leu
                165                 170                 175

Ala Arg Asp Gly Phe Ile Val Asn Asp Ala Leu Ala Asp Asp Leu Lys
            180                 185                 190

Thr Tyr Gly Ser Glu Val Leu Pro Asn His Glu Asn Ser Lys Ala Ile
        195                 200                 205

Phe Trp Lys Glu Gly Glu Pro Leu Lys Lys Gly Asp Thr Leu Val Gln
    210                 215                 220

Ala Asn Leu Ala Lys Ser Leu Glu Met Ile Ala Glu Asn Gly Pro Asp
225                 230                 235                 240

Glu Phe Tyr Lys Gly Thr Ile Ala Glu Gln Ile Ala Gln Glu Met Gln
                245                 250                 255

Lys Asn Gly Gly Leu Ile Thr Lys Glu Asp Leu Ala Ala Tyr Lys Ala
            260                 265                 270

Val Glu Arg Thr Pro Ile Ser Gly Asp Tyr Arg Gly Tyr Gln Val Tyr
        275                 280                 285

Ser Met Pro Pro Pro Ser Ser Gly Gly Ile His Ile Val Gln Ile Leu
    290                 295                 300

Asn Ile Leu Glu Asn Phe Asp Met Lys Lys Tyr Gly Phe Gly Ser Ala
305                 310                 315                 320

Asp Ala Met Gln Ile Met Ala Glu Ala Glu Lys Tyr Ala Tyr Ala Asp
                325                 330                 335

Arg Ser Glu Tyr Leu Gly Asp Pro Asp Phe Val Lys Val Pro Trp Gln
            340                 345                 350

Ala Leu Thr Asn Lys Ala Tyr Ala Lys Ser Ile Ala Asp Gln Ile Asp
        355                 360                 365

Ile Asn Lys Ala Lys Pro Ser Ser Glu Ile Arg Pro Gly Lys Leu Ala
    370                 375                 380
```

```
Pro Tyr Glu Ser Asn Gln Thr Thr His Tyr Ser Val Val Asp Lys Asp
385                 390                 395                 400

Gly Asn Ala Val Ala Val Thr Tyr Thr Leu Asn Thr Thr Phe Gly Thr
                405                 410                 415

Gly Ile Val Ala Gly Glu Ser Gly Ile Leu Leu Asn Asn Gln Met Asp
            420                 425                 430

Asp Phe Ser Ala Lys Pro Gly Val Pro Asn Val Tyr Gly Leu Val Gly
        435                 440                 445

Gly Asp Ala Asn Ala Val Gly Pro Asn Lys Arg Pro Leu Ser Ser Met
    450                 455                 460

Ser Pro Thr Ile Val Val Lys Asp Gly Lys Thr Trp Leu Val Thr Gly
465                 470                 475                 480

Ser Pro Gly Gly Ser Arg Ile Ile Thr Thr Val Leu Gln Met Val Val
                485                 490                 495

Asn Ser Ile Asp Tyr Gly Leu Asn Val Ala Glu Ala Thr Asn Ala Pro
            500                 505                 510

Arg Phe His His Gln Trp Leu Pro Asp Glu Leu Arg Val Glu Lys Gly
        515                 520                 525

Phe Ser Pro Asp Thr Leu Lys Leu Leu Glu Ala Lys Gly Gln Lys Val
    530                 535                 540

Ala Leu Lys Glu Ala Met Gly Ser Thr Gln Ser Ile Met Val Gly Pro
545                 550                 555                 560

Asp Gly Glu Leu Tyr Gly Ala Ser Asp Pro Arg Ser Val Asp Asp Leu
                565                 570                 575

Thr Ala Gly Tyr
            580

<210> SEQ ID NO 3
<211> LENGTH: 1458
<212> TYPE: DNA
<213> ORGANISM: Escherichia coli
<220> FEATURE:
<221> NAME/KEY: CDS
<222> LOCATION: (1)..(1458)

<400> SEQUENCE: 3 gtg tct gaa ctg tct caa tta tct cca cag ccg ctg tgg gat att ttt     48
Val Ser Glu Leu Ser Gln Leu Ser Pro Gln Pro Leu Trp Asp Ile Phe
1               5                   10                  15 gcc aaa atc tgt tct att cct cac ccg tcc tat cat gaa gag caa ctc     96
Ala Lys Ile Cys Ser Ile Pro His Pro Ser Tyr His Glu Glu Gln Leu
            20                  25                  30 gct gaa tac att gtt ggt tgg gca aaa gag aaa ggt ttc cat gtc gaa    144
Ala Glu Tyr Ile Val Gly Trp Ala Lys Glu Lys Gly Phe His Val Glu
        35                  40                  45 cgc gat cag gta ggt aat atc ctg att cgt aaa cct gct acc gca ggt    192
Arg Asp Gln Val Gly Asn Ile Leu Ile Arg Lys Pro Ala Thr Ala Gly
    50                  55                  60 atg gaa aat cgt aaa ccg gtc gtc tta cag gcc cac ctc gat atg gtg    240
Met Glu Asn Arg Lys Pro Val Val Leu Gln Ala His Leu Asp Met Val
65                  70                  75                  80 ccg cag aaa aat aac gac acc gtg cat gac ttc acg aaa gat cct atc    288
Pro Gln Lys Asn Asn Asp Thr Val His Asp Phe Thr Lys Asp Pro Ile
                85                  90                  95 cag cct tat att gat ggc gaa tgg gtt aaa gcg cgc ggc acc acg ctg    336
Gln Pro Tyr Ile Asp Gly Glu Trp Val Lys Ala Arg Gly Thr Thr Leu
            100                 105                 110
```

```
ggt gcg gat aac ggt att ggt atg gcc tct gcg ctg gcg gtt ctg gct    384
Gly Ala Asp Asn Gly Ile Gly Met Ala Ser Ala Leu Ala Val Leu Ala
        115                 120                 125 gac gaa aac gtg gtt cac ggc ccg ctg gaa gtg ctg ctg acc atg acc    432
Asp Glu Asn Val Val His Gly Pro Leu Glu Val Leu Leu Thr Met Thr
130                 135                 140 gaa gaa gcc ggt atg gac ggt gcg ttc ggc tta cag ggc aac tgg ttg    480
Glu Glu Ala Gly Met Asp Gly Ala Phe Gly Leu Gln Gly Asn Trp Leu
145                 150                 155                 160 cag gct gat att ctg att aac acc gac tcc gaa gaa gaa ggt gaa atc    528
Gln Ala Asp Ile Leu Ile Asn Thr Asp Ser Glu Glu Glu Gly Glu Ile
            165                 170                 175 tac atg ggt tgt gcg ggg ggt atc gac ttc acc tcc aac ctg cat tta    576
Tyr Met Gly Cys Ala Gly Gly Ile Asp Phe Thr Ser Asn Leu His Leu
                180                 185                 190 gat cgt gaa gcg gtt cca gct ggt ttt gaa acc ttc aag tta acc tta    624
Asp Arg Glu Ala Val Pro Ala Gly Phe Glu Thr Phe Lys Leu Thr Leu
            195                 200                 205 aaa ggt ctg aaa ggc ggt cac tcc ggc ggg gaa atc cac gtt ggg ctg    672
Lys Gly Leu Lys Gly Gly His Ser Gly Gly Glu Ile His Val Gly Leu
        210                 215                 220 ggt aat gcc aac aaa ctg ctg gtg cgc ttc ctg gcg ggt cat gcg gaa    720
Gly Asn Ala Asn Lys Leu Leu Val Arg Phe Leu Ala Gly His Ala Glu
225                 230                 235                 240 gaa ctg gat ctg cgc ctt atc gat ttc aac ggc ggc aca ctg cgt aac    768
Glu Leu Asp Leu Arg Leu Ile Asp Phe Asn Gly Gly Thr Leu Arg Asn
            245                 250                 255 gcc atc ccg cgt gaa gcc ttt gcg acc att gct gtc gca gct gat aaa    816
Ala Ile Pro Arg Glu Ala Phe Ala Thr Ile Ala Val Ala Ala Asp Lys
                260                 265                 270 gtc gac gtc ctg aaa tct ctg gtg aat acc tat cag gag atc ctg aaa    864
Val Asp Val Leu Lys Ser Leu Val Asn Thr Tyr Gln Glu Ile Leu Lys
            275                 280                 285 aac gag ctg gca gaa aaa gag aaa aat ctg gcc ttg ttg ctg gac tct    912
Asn Glu Leu Ala Glu Lys Glu Lys Asn Leu Ala Leu Leu Leu Asp Ser
        290                 295                 300 gta gcg aac gat aaa gct gcc ctg att gcg aaa tct cgc gat acc ttt    960
Val Ala Asn Asp Lys Ala Ala Leu Ile Ala Lys Ser Arg Asp Thr Phe
305                 310                 315                 320 att cgt ctg ctg aac gcc acc ccg aac ggt gtg att cgt aac tcc gat   1008
Ile Arg Leu Leu Asn Ala Thr Pro Asn Gly Val Ile Arg Asn Ser Asp
            325                 330                 335 gta gcc aaa ggt gtg gtt gaa acc tcc ctg aac gtc ggt gtg gtg acc   1056
Val Ala Lys Gly Val Val Glu Thr Ser Leu Asn Val Gly Val Val Thr
                340                 345                 350 atg act gac aat aac gta gaa att cac tgc ctg atc cgt tca ctg atc   1104
Met Thr Asp Asn Asn Val Glu Ile His Cys Leu Ile Arg Ser Leu Ile
            355                 360                 365 gac agc ggt aaa gac tac gtg gtg agc atg ctg gat tcg ctg ggt aaa   1152
Asp Ser Gly Lys Asp Tyr Val Val Ser Met Leu Asp Ser Leu Gly Lys
        370                 375                 380 ctg gct ggc gcg aaa acc gaa gcg aaa ggc gca tat cct ggc tgg cag   1200
Leu Ala Gly Ala Lys Thr Glu Ala Lys Gly Ala Tyr Pro Gly Trp Gln
385                 390                 395                 400 ccg gac gct aat tct ccg gtg atg cat ctg gta cgt gaa acc tat cag   1248
Pro Asp Ala Asn Ser Pro Val Met His Leu Val Arg Glu Thr Tyr Gln
            405                 410                 415 cgc ctg ttc aac aag acg ccg aac atc cag att atc cac gcg ggc ctg   1296
Arg Leu Phe Asn Lys Thr Pro Asn Ile Gln Ile Ile His Ala Gly Leu
            420                 425                 430
```

-continued

```
gaa tgt ggt ctg ttc aaa aaa ccg tat ccg gaa atg gac atg gtt tct    1344
Glu Cys Gly Leu Phe Lys Lys Pro Tyr Pro Glu Met Asp Met Val Ser
        435                 440                 445 atc ggg cca act atc acc ggt cca cac tct ccg gat gag caa gtt cac    1392
Ile Gly Pro Thr Ile Thr Gly Pro His Ser Pro Asp Glu Gln Val His
450                 455                 460 atc gaa agc gta ggt cat tac tgg aca ctg ctg act gaa ctg ctg aaa    1440
Ile Glu Ser Val Gly His Tyr Trp Thr Leu Leu Thr Glu Leu Leu Lys
465                 470                 475                 480 gaa att ccg gcg aag taa                                            1458
Glu Ile Pro Ala Lys
                485
```

<210> SEQ ID NO 4
<211> LENGTH: 485
<212> TYPE: PRT
<213> ORGANISM: Escherichia coli

<400> SEQUENCE: 4

```
Val Ser Glu Leu Ser Gln Leu Ser Pro Gln Pro Leu Trp Asp Ile Phe
1               5                   10                  15

Ala Lys Ile Cys Ser Ile Pro His Pro Ser Tyr His Glu Glu Gln Leu
            20                  25                  30

Ala Glu Tyr Ile Val Gly Trp Ala Lys Glu Lys Gly Phe His Val Glu
        35                  40                  45

Arg Asp Gln Val Gly Asn Ile Leu Ile Arg Lys Pro Ala Thr Ala Gly
    50                  55                  60

Met Glu Asn Arg Lys Pro Val Val Leu Gln Ala His Leu Asp Met Val
65                  70                  75                  80

Pro Gln Lys Asn Asn Asp Thr Val His Asp Phe Thr Lys Asp Pro Ile
                85                  90                  95

Gln Pro Tyr Ile Asp Gly Glu Trp Val Lys Ala Arg Gly Thr Thr Leu
            100                 105                 110

Gly Ala Asp Asn Gly Ile Gly Met Ala Ser Ala Leu Ala Val Leu Ala
        115                 120                 125

Asp Glu Asn Val Val His Gly Pro Leu Glu Val Leu Leu Thr Met Thr
    130                 135                 140

Glu Glu Ala Gly Met Asp Gly Ala Phe Gly Leu Gln Gly Asn Trp Leu
145                 150                 155                 160

Gln Ala Asp Ile Leu Ile Asn Thr Asp Ser Glu Glu Gly Glu Ile
                165                 170                 175

Tyr Met Gly Cys Ala Gly Gly Ile Asp Phe Thr Ser Asn Leu His Leu
            180                 185                 190

Asp Arg Glu Ala Val Pro Ala Gly Phe Glu Thr Phe Lys Leu Thr Leu
        195                 200                 205

Lys Gly Leu Lys Gly Gly His Ser Gly Gly Glu Ile His Val Gly Leu
    210                 215                 220

Gly Asn Ala Asn Lys Leu Leu Val Arg Phe Leu Ala Gly His Ala Glu
225                 230                 235                 240

Glu Leu Asp Leu Arg Leu Ile Asp Phe Asn Gly Gly Thr Leu Arg Asn
                245                 250                 255

Ala Ile Pro Arg Glu Ala Phe Ala Thr Ile Ala Val Ala Ala Asp Lys
            260                 265                 270

Val Asp Val Leu Lys Ser Leu Val Asn Thr Tyr Gln Glu Ile Leu Lys
        275                 280                 285
```

```
Asn Glu Leu Ala Glu Lys Glu Lys Asn Leu Ala Leu Leu Asp Ser
        290                 295                 300

Val Ala Asn Asp Lys Ala Ala Leu Ile Ala Lys Ser Arg Asp Thr Phe
305                 310                 315                 320

Ile Arg Leu Leu Asn Ala Thr Pro Asn Gly Val Ile Arg Asn Ser Asp
                325                 330                 335

Val Ala Lys Gly Val Val Glu Thr Ser Leu Asn Val Gly Val Val Thr
            340                 345                 350

Met Thr Asp Asn Asn Val Glu Ile His Cys Leu Ile Arg Ser Leu Ile
        355                 360                 365

Asp Ser Gly Lys Asp Tyr Val Val Ser Met Leu Asp Ser Leu Gly Lys
        370                 375                 380

Leu Ala Gly Ala Lys Thr Glu Ala Lys Gly Ala Tyr Pro Gly Trp Gln
385                 390                 395                 400

Pro Asp Ala Asn Ser Pro Val Met His Leu Val Arg Glu Thr Tyr Gln
                405                 410                 415

Arg Leu Phe Asn Lys Thr Pro Asn Ile Gln Ile Ile His Ala Gly Leu
                420                 425                 430

Glu Cys Gly Leu Phe Lys Lys Pro Tyr Pro Glu Met Asp Met Val Ser
        435                 440                 445

Ile Gly Pro Thr Ile Thr Gly Pro His Ser Pro Asp Glu Gln Val His
        450                 455                 460

Ile Glu Ser Val Gly His Tyr Trp Thr Leu Leu Thr Glu Leu Leu Lys
465                 470                 475                 480

Glu Ile Pro Ala Lys
                485

<210> SEQ ID NO 5
<211> LENGTH: 23
<212> TYPE: DNA
<213> ORGANISM: Artificial Sequence
<220> FEATURE:
<223> OTHER INFORMATION: synthetic primer

<400> SEQUENCE: 5
cacaccgcat aaggtgcact ctc                                            23

<210> SEQ ID NO 6
<211> LENGTH: 23
<212> TYPE: DNA
<213> ORGANISM: Artificial Sequence
<220> FEATURE:
<223> OTHER INFORMATION: synthetic primer

<400> SEQUENCE: 6
gagagtgcac cttatgcggt gtg                                            23

<210> SEQ ID NO 7
<211> LENGTH: 27
<212> TYPE: DNA
<213> ORGANISM: Artificial Sequence
<220> FEATURE:
<223> OTHER INFORMATION: synthetic primer

<400> SEQUENCE: 7
gtaaggagga atgcatatga aaaatac                                        27
```

<210> SEQ ID NO 8
<211> LENGTH: 27
<212> TYPE: DNA
<213> ORGANISM: Artificial Sequence
<220> FEATURE:
<223> OTHER INFORMATION: synthetic primer

<400> SEQUENCE: 8
gtatttttca tatgcattcc tccttac                                          27

<210> SEQ ID NO 9
<211> LENGTH: 29
<212> TYPE: DNA
<213> ORGANISM: Artificial Sequence
<220> FEATURE:
<223> OTHER INFORMATION: synthetic primer

<400> SEQUENCE: 9
gctctagaag tttgatatca atggcttat                                        29

<210> SEQ ID NO 10
<211> LENGTH: 45
<212> TYPE: DNA
<213> ORGANISM: Artificial Sequence
<220> FEATURE:
<223> OTHER INFORMATION: synthetic primer

<400> SEQUENCE: 10
gggaattcca tatgcattcc tccttaatcg atatcttctg gcgct                      45

<210> SEQ ID NO 11
<211> LENGTH: 37
<212> TYPE: DNA
<213> ORGANISM: Artificial Sequence
<220> FEATURE:
<223> OTHER INFORMATION: synthetic primer

<400> SEQUENCE: 11
gggaattcca tatgataaaa ccgacgtttt tacgccg                               37

<210> SEQ ID NO 12
<211> LENGTH: 37
<212> TYPE: DNA
<213> ORGANISM: Artificial Sequence
<220> FEATURE:
<223> OTHER INFORMATION: synthetic primer

<400> SEQUENCE: 12
aaaactgcag ttagtacccc gccgttaaat catccac                               37

<210> SEQ ID NO 13
<211> LENGTH: 54
<212> TYPE: DNA
<213> ORGANISM: Artificial Sequence
<220> FEATURE:
<223> OTHER INFORMATION: synthetic primer

<400> SEQUENCE: 13
gtgtctgaac tgtctcaatt atctccacag ccgctgtgaa gcctgctttt ttat            54

<210> SEQ ID NO 14
<211> LENGTH: 54
<212> TYPE: DNA
<213> ORGANISM: Artificial Sequence
<220> FEATURE:
<223> OTHER INFORMATION: synthetic primer -continued

```
<400> SEQUENCE: 14
cttcgccgga atttctttca gcagttcagt cagcagcgct caagttagta taaa            54
```

METHOD FOR PRODUCING γ-GLUTAMYL-VALYL-GLYCINE CRYSTAL

TECHNICAL FIELD

The present invention relates to a method for producing a γ-glutamyl-valyl-glycine crystal. More specifically, the present invention relates to a method for efficiently producing a γ-glutamyl-valyl-glycine crystal by adjusting the amount of residual valyl-glycine or a salt thereof in a mixed solution of valyl-glycine or the salt thereof and γ-glutamyl-valyl-glycine obtained by the enzyme reaction between valyl-glycine or the salt thereof and a γ-glutamyl group donor.

BACKGROUND ART

γ-Glutamyl-valyl-glycine (γ-Glu-Val-Gly) has been known as a peptide giving rich flavor to food (Patent Literature 1). γ-Glutamyl-valyl-glycine is, for example, produced by chemical synthesis methods or enzymatic methods. Among them, when γ-glutamyl-valyl-glycine is produced by enzymatic methods, for example, valyl-glycine or a salt thereof is reacted with a glutamyl group donor, such as glutamine, in the presence of γ-glutamyl transferase (hereinafter, γ-glutamyl transferase is also referred to as "GGT") to produce a solution containing γ-glutamyl-valyl-glycine, and then γ-glutamyl-valyl-glycine is obtained from the solution (Non Patent Literature 1).

CITATION LIST

Patent Literature

Patent Literature 1: WO 2007/055393

Non Patent Literature

Non Patent Literature 1: Suzuki, H. et al., (2008) Improvement of the flavor of amino acids and peptides using bacterial γ-glutamyltranspeptidase. In Recent High lights in Flavor Chemistry & Biology, Ed. by Hofmann, T. et al., p. 227-232, Deutsche Forschungsanstalt fur Lebensmittelchemie

SUMMARY OF INVENTION

Technical Problems

The present inventors attempted to crystallize γ-glutamyl-valyl-glycine from a γ-glutamyl-valyl-glycine solution containing valyl-glycine and as a result, found a problem that a γ-glutamyl-valyl-glycine solution containing a large amount of residual valyl-glycine or salt thereof often gelled to prevent crystallization.

Therefore, the present invention aims at providing a method for efficiently producing a γ-glutamyl-valyl-glycine crystal.

The present invention also aims at providing a method for producing a γ-glutamyl-valyl-glycine crystal having a larger crystal size.

The present invention aims at providing a method for efficiently producing a γ-glutamyl-valyl-glycine crystal.

Solution to Problems

The present inventors have found that formation of the γ-glutamyl-valyl-glycine crystal after adjusting the residual amount of valyl-glycine causes no problem with gelation and accordingly efficiently provides the γ-glutamyl-valyl-glycine crystal in a method for producing the γ-glutamyl-valyl-glycine crystal from a γ-glutamyl-valyl-glycine solution containing valyl-glycine, for example, a method for producing γ-glutamyl-valyl-glycine by an enzymatic method using valyl-glycine as a starting material, thereby completing the present invention. The present inventors also have found that the γ-glutamyl-valyl-glycine crystal formed by the above method has a larger crystal size than those obtained by conventional methods.

Specifically, the present invention may have the following characteristics.

[1] A method for producing a γ-glutamyl-valyl-glycine crystal, the method comprising the steps of:

reacting valyl-glycine or a salt thereof with a γ-glutamyl group donor in the presence of γ-glutamyl transferase or a microorganism containing the enzyme to prepare a mixed solution of valyl-glycine or the salt thereof and γ-glutamyl-valyl-glycine, in which the mixed solution contains valyl-glycine in an amount of 20 mass % or more relative to the mass of γ-glutamyl-valyl-glycine;

adjusting the amount of valyl-glycine or the salt thereof in the prepared mixed solution to 0.1 mass % or more and less than 20 mass % relative to the mass of γ-glutamyl-valyl-glycine in the solution to prepare a γ-glutamyl-valyl-glycine solution; and subjecting the γ-glutamyl-valyl-glycine solution to a crystallization procedure to produce the γ-glutamyl-valyl-glycine crystal.

[2] The method according to [1] above, wherein the amount of valyl-glycine or the salt thereof in the mixed solution is adjusted in the range of from 1 to 18 mass % relative to the mass of γ-glutamyl-valyl-glycine in the solution.

[3] The method according to [1] or [2] above, wherein the amount of valyl-glycine or the salt thereof in the mixed solution is adjusted by adsorbing γ-glutamyl-valyl-glycine in the mixed solution to an adsorption resin and allowing valyl-glycine or the salt thereof in the mixed solution to flow through the adsorption resin, followed by elution of γ-glutamyl-valyl-glycine from the adsorption resin.

[4] The method according to any one of [1] to [3] above, wherein the γ-glutamyl group donor is glutamine.

[5] The method according to any one of [1] to [4] above, wherein γ-glutamyl transferase or the microorganism containing the enzyme is a bacterium belonging to the Enterobacteriaceae.

[6] The method according to [5] above, wherein the bacterium is *Escherichia coli*.

[7] The method according to any one of [1] to [6], wherein valyl-glycine or the salt thereof is reacted with the γ-glutamyl group donor in a solvent selected from water and buffers.

[8] A γ-glutamyl-valyl-glycine crystal, containing at least one selected from valyl-valine, salts of valyl-valine, valyl-valyl-glycine, and salts of valyl-valyl-glycine in an amount of 2.0 mass % or less, wherein the crystal having a longitudinal length of 35 μm or more has a mean of the transverse diameter of 2.1 μm or more.

[9] The γ-glutamyl-valyl-glycine crystal according to [8] above, wherein the crystal having a longitudinal length of 35 μm or more has a mean of the transverse diameter of 2.1 μm or more among γ-glutamyl-valyl-glycine crystals whose entire images are included in the region of 415 μm×332 μm in the image taken with an optical microscope.

[10] The γ-glutamyl-valyl-glycine crystal according to [8] or [9] above, comprising 3 mass % or less of valyl-glycine.

The present invention can efficiently produce a γ-glutamyl-valyl-glycine crystal.

The present invention can also produce a γ-glutamyl-valyl-glycine crystal having a larger crystal size.

The present invention provides a larger crystal and thus achieves excellent treatment processes more suitable to industrial treatments.

DESCRIPTION OF EMBODIMENTS

[1] Method for Producing γ-Glutamyl-Valyl-Glycine Crystal

Figure 1:
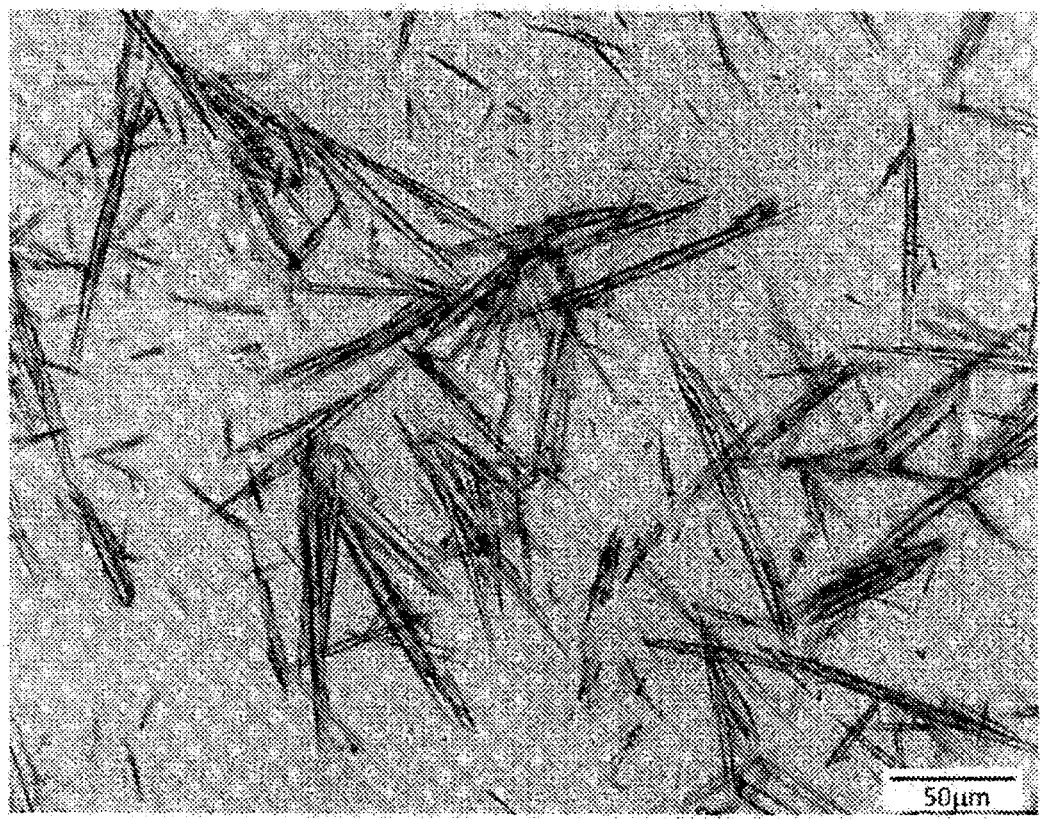
FIG. 1 shows an optical micrograph of the γ-glutamyl-valyl-glycine crystals of the present invention, obtained when the concentration of valyl-glycine is 10 mass % (Example 6).
Figure 2:
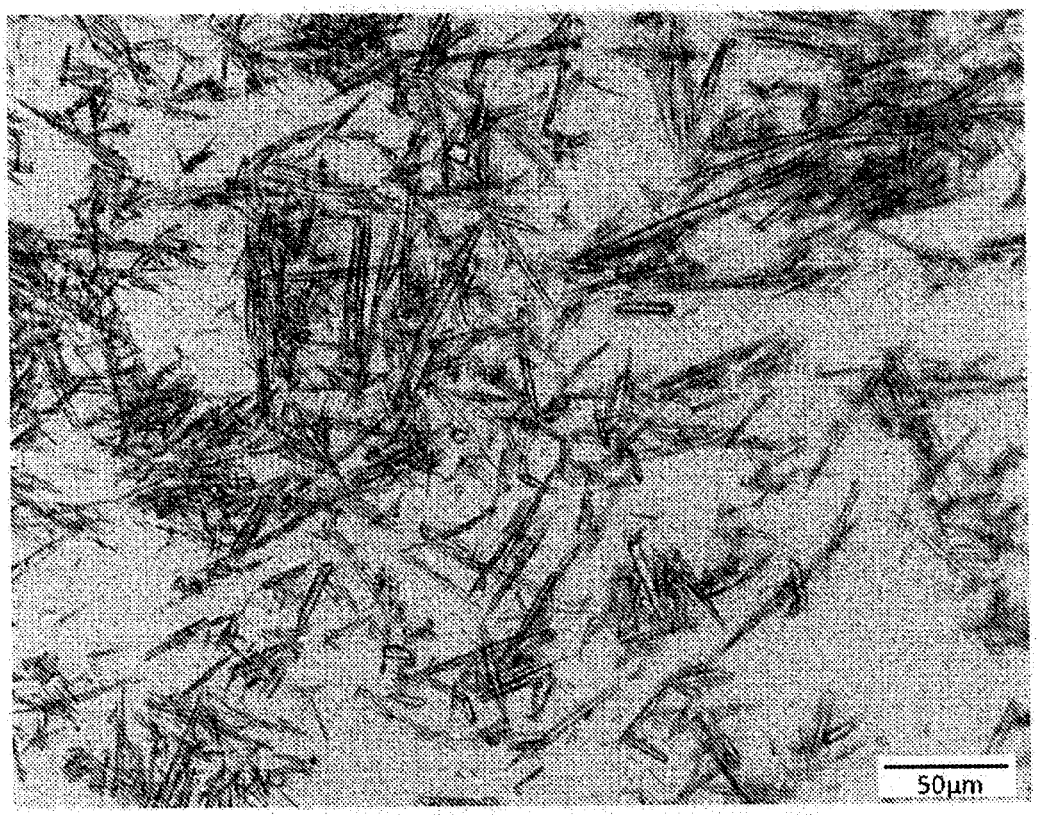
FIG. 2 shows an optical micrograph of the γ-glutamyl-valyl-glycine crystals of the present invention, obtained when the concentration of valyl-glycine is 15 mass % (Example 7).
Figure 3:
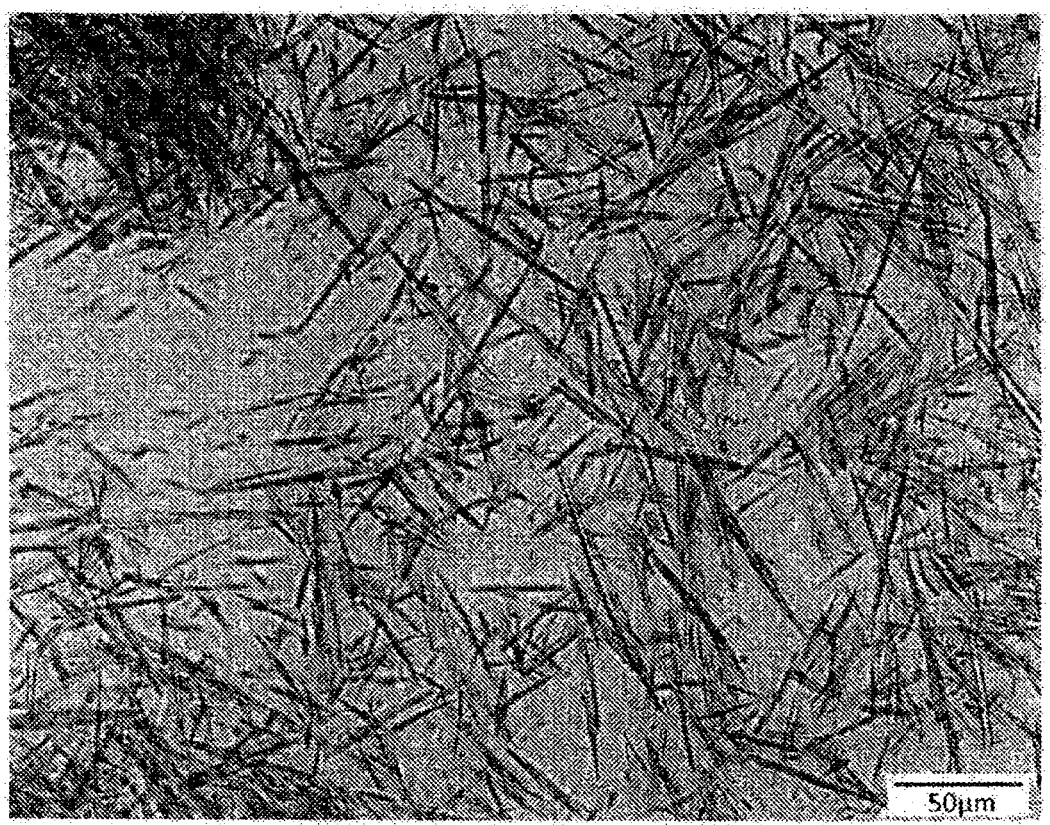
FIG. 3 shows an optical micrograph of γ-glutamyl-valyl-glycine crystals, obtained when the concentration of valyl-glycine is 20 mass % (Comparative Example 2).
Figure 4:
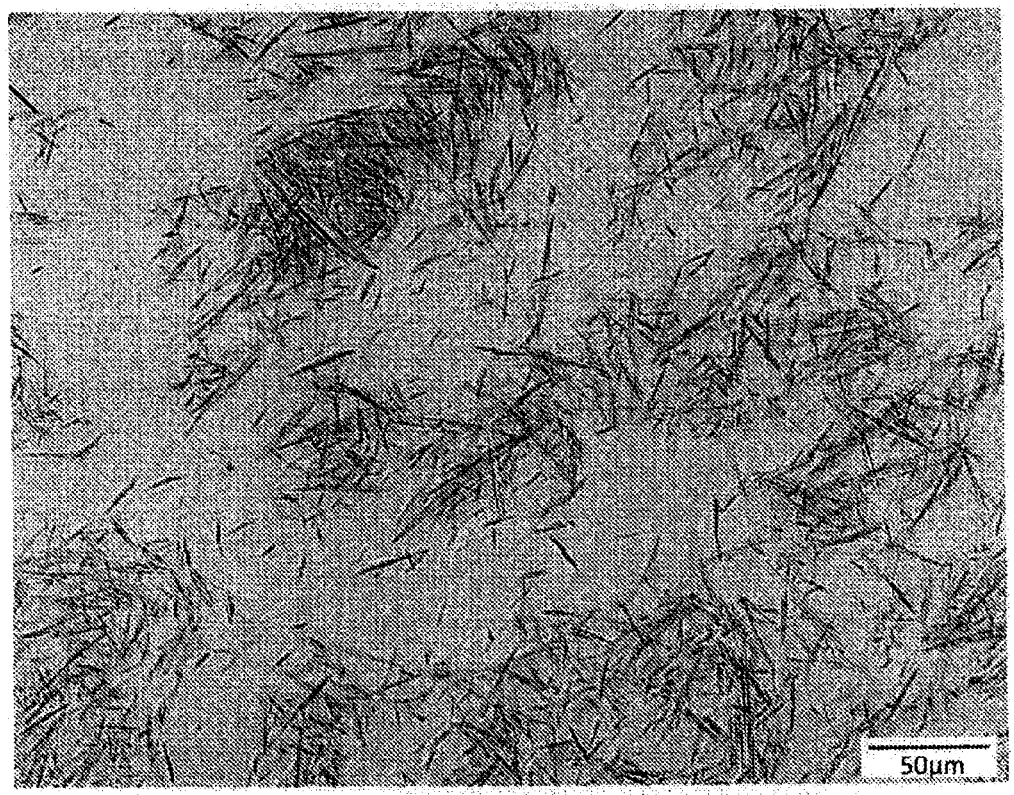
FIG. 4 shows an optical micrograph of γ-glutamyl-valyl-glycine crystals, obtained when the concentration of valyl-glycine is 25 mass % (Comparative Example 3).

The present invention may relate to a method for producing a γ-glutamyl-valyl-glycine crystal, wherein the method comprises the steps of:

(1) reacting valyl-glycine or a salt thereof with a γ-glutamyl group donor in the presence of γ-glutamyl transferase or a microorganism containing the enzyme to prepare a mixed solution of valyl-glycine or the salt thereof and γ-glutamyl-valyl-glycine;

(2) adjusting the amount of valyl-glycine or the salt thereof in the prepared mixed solution to 0.1 mass % or more and less than 20 mass % relative to the mass of γ-glutamyl-valyl-glycine to prepare a γ-glutamyl-valyl-glycine solution; and (3) subjecting the γ-glutamyl-valyl-glycine solution to a crystallization procedure to produce the γ-glutamyl-valyl-glycine crystal.

(1) Step of Preparing γ-Glutamyl-Valyl-Glycine Mixed Solution

The step of preparing a γ-glutamyl-valyl-glycine mixed solution include, for example, (a) a process of reacting valyl-glycine or a salt thereof with a γ-glutamyl group donor in the presence of γ-glutamyl transferase or a microorganism containing the enzyme to prepare a mixed solution of valyl-glycine or the salt thereof and γ-glutamyl-valyl-glycine; (b) a process of reacting γ-glutamyl-valine with glycine in the presence of glutathione synthetase or a microorganism containing the enzyme to produce γ-glutamyl-valyl-glycine, as described in Japanese Patent Application Laid-Open (JP-A) No. 2012-85637 (this literature is incorporated herein by reference), and further decomposing γ-glutamyl-valyl-glycine with γ-glutamyl transferase or γ-glutamyl transferase of a microorganism containing the enzyme to produce valyl-glycine in a reaction liquid, thereby preparing a mixed solution of valyl-glycine or the salt thereof and γ-glutamyl-valyl-glycine; and further (c) a process of heating a solution produced by synthesizing γ-glutamyl-valyl-glycine, under acid in industrial processing, which may generate valyl-glycine. Any of these processes can be applied to the method for producing a crystal of the present invention. Among these, preferred is process (a) of reacting valyl-glycine or a salt thereof with a γ-glutamyl group donor in the presence of γ-glutamyl transferase or a microorganism containing the enzyme to prepare a mixed solution of valyl-glycine or the salt thereof and γ-glutamyl-valyl-glycine. Process (a) will be described below in detail.

In general, the reaction between valyl-glycine and a γ-glutamyl group donor with γ-glutamyl transferase ideally provides a mixed solution of valyl-glycine or the salt thereof and γ-glutamyl-valyl-glycine where the rearrangement reaction has proceeded efficiently. It is generally known that the reaction efficiency of the rearrangement reaction with γ-glutamyl transferase usually depends on the acceptor or the ratio of acceptors to γ-glutamyl group donors, and unreacted acceptors remain in the rearrangement reaction [Suzuki H. et al., γ-Glutamyl compounds and their enzymatic production using bacterial γ-glutamyltranspeptidase, Amino acids, 32: 333-340, 2007 (this literature is incorporated herein by reference)]. When valyl-glycine is used as the acceptor, unreacted valyl-glycine also remains in the reaction solution. The amount of residual unreacted valyl-glycine depends on the yield. The relationship between approximate reaction yield and residual valyl-glycine amount is such that about 30% yield results in about 134 mass % of the mass ratio of valyl-glycine to γ-glutamyl-valyl-glycine, and about 70% yield results in about 25 mass % of the mass ratio.

Specifically, the mass ratio of valyl-glycine to γ-glutamyl-valyl-glycine in the mixed solution is, for example, 20 mass % or more, preferably form 25 to 850 mass %, preferably from 30 to 134 mass %, more preferably from 40 to 86 mass %. Here, the mass % is the value based on the free forms. The "based on the free forms" means that, when valyl-glycine and γ-glutamyl-valyl-glycine form salts in the mixture, the mass of valyl-glycine and γ-glutamyl-valyl-glycine is expressed based on their free forms (not salt forms).

The amount of γ-glutamyl-valyl-glycine or the salt thereof in the mixed solution here is, for example, from 0.05 to 50 mass %, preferably 0.1 to 50 mass %, more preferably 0.5 to 50 mass %, as being expressed based on the free form.

γ-Glutamyl transferase (GGT) is composed of a large subunit and a small subunit. GGT may be a wild-type or mutant. Here, amino acids are L-amino acids unless otherwise specified.

Wild-type GGTs include GGT encoded by the ggt gene of *Escherichia coli* and their homologues, for example, GGT of *Escherichia coli*, and GGTs of other microorganisms, especially having a similar small subunit structure.

The nucleotide sequence of the ggt gene of the *Escherichia coli* K-12 strain is described in JP-A No. 02-231085 (this literature is incorporated herein by reference). The nucleotide sequence of the ggt gene of the *Escherichia coli* K-12 W3110 strain is registered in the database as 4053592 . . . 4055334 of GenBank accession AP009048. The nucleotide sequence of this ggt gene is shown in SEQ ID NO: 1. The amino acid sequence encoded by this nucleotide sequence is shown in SEQ ID NO: 2. In SEQ ID NO: 2, positions 1 to 25 correspond to the leader peptide, positions 26 to 390 correspond to the large subunit, and positions 391 to 580 correspond to the small subunit.

GGT homologues homologous to GGT of *Escherichia coli* preferably include a small subunit having an amino acid sequence with a homology of 90% or more to the site (positions 391 to 580) corresponding to the small subunit in the amino acid sequence of SEQ ID NO: 2. The GGT homologues preferably contain a large subunit having an amino acid sequence with a homology of 90% or more to the site (positions 26 to 390) corresponding to the large subunit in the amino acid sequence of SEQ ID NO: 2.

As γ-glutamyl transferase (GGT) or microorganisms containing the enzyme, for example, *Escherichia* bacteria, such as *Escherichia coli*; gram-negative bacteria, such as *Enterobacter* bacteria and *Pantoea* bacteria; gram-positive bacteria, such as *Bacillus* bacteria; *Corynebacterium* bacteria, and other bacteria can be used.

As GGT or microorganisms containing the enzyme, processed products of GGT or microorganisms containing the enzyme, i.e., for example, disrupted cells, cell extracts, partially purified products thereof, or purified enzymes, as well as cells obtained by immobilizing the processed products with acrylamide, carrageenan, or other materials, or immobilized enzymes obtained by immobilizing GGT on a solid support such as resin or others can be used.

Specific examples of GGT or microorganisms containing the enzyme include GGT of bacteria belonging to the Enterobacteriaceae. Bacteria belonging to the Enterobacteriaceae include, but are not limited to, bacteria belonging to the genera of *Escherichia, Enterobacter, Erwinia, Klebsiella, Pantoea, Photorhabdus, Providencia, Salmonella, Serratia, Shigella, Morganella, Yersinia*, and other genera. In particular, bacteria classified into the Enterobacteriaceae according to the taxonomy used in the NCBI (National Center for Biotechnology Information) database (http://www.ncbi.nlm.nih.gov/Taxonomy/Browser/wwwtax.cgi?id=91347) are preferred. Specific examples of bacteria belonging to the Enterobacteriaceae include *Escherichia coli, Shigella flexneri, Shigella dysenteriae, Shigella boydii, Salmonella typhimurium, Klebsiella pneumoniae, Salmonella enterica*, and *Enterobacter cloacae*.

GGT or microorganisms containing the enzyme can be produced by culturing microorganisms transfected with the ggt gene in an expressible form under conditions allowing expression of the gene to grow the cells. The medium used for the culture is not particularly limited so long as the target microorganism can grow in it, and there can be used an ordinary medium containing a carbon source, nitrogen source, sulfur source, inorganic ions, and other optional organic components.

As the carbon source, saccharides, such as glucose, fructose, sucrose, glycerol, ethanol, molasses and starch hydrolysate; and organic acids, such as fumaric acid, citric acid, and succinic acid can be used. As the nitrogen source, inorganic ammonium salts, such as ammonium sulfate, ammonium chloride, and ammonium phosphate; organic nitrogen, such as soybean hydrolysate; ammonia gas, aqueous ammonia, and others can be used. The sulfur sources include inorganic sulfur compounds, such as sulfates, sulfites, sulfides, hyposulfites, and thiosulfates. As organic micronutrients, a proper amount of required substance, such as vitamin B1, or yeast extract, or the like is preferably contained in the medium. In addition to these, potassium phosphate, magnesium sulfate, iron ions, manganese ions, or others are added in a small amount as desired.

The culture conditions can be appropriately set according to the microorganism to be used. The microorganism is preferably cultured, for example, at a culture temperature of from 20 to 45° C., preferably from 24 to 45° C. The culture is preferably aerobic culture at an oxygen concentration of from to 50 vol %, desirably about 10 vol %, with respect to the saturated concentration. The pH during the culture is preferably from 5.0 to 9.0. For pH adjustment, inorganic or organic, acidic or alkaline substances, e.g., calcium carbonate, ammonia gas, and aqueous ammonia, can be used. The culture time is preferably about 10 to 120 hours.

GGT can be used while being included in cells, or may be used as a crude enzyme fraction or purified enzyme extracted from the cells. GGT can be extracted by the same method as ordinary extraction of periplasmic enzymes, for example, osmotic shock method, and freezing and thawing method.

(GGT can be purified by appropriate combination of procedures usually used for purification of enzymes, such as ammonium sulfate fractionation, ion exchange chromatography, hydrophobic chromatography, affinity chromatography, gel filtration chromatography, and isoelectric precipitation. When GGT is secreted out of cells, GGT collected from the medium can be used.

As γ-glutamyl transferase (GGT) or microorganisms containing the enzyme in the present invention, processed products of GGT or microorganisms, such as disrupted cells, cell extracts, partially purified products thereof, or purified enzymes, as well as cells obtained by immobilizing the processed products with acrylamide, carrageenan, or others, or immobilized enzymes obtained by immobilizing mutant GGT on a resin or others may be used.

Valyl-glycine (Val-Gly) or a salt thereof can be produced by various known procedures. For example, it can be also produce by a chemical synthesis method using formyl-L-valine and glycine ethyl ester as materials (Journal of the American Chemical Society (1958), 80, pp. 1154-1158 (this literature is incorporated herein by reference)). For this production, a chemical synthesis method using N-carboxy-anhydride of valine (valine-NCA) and glycine as materials can be also used (Canadian Journal of Chemistry (1973), 51 (8), pp. 1284-87 (this literature is incorporated herein by reference)). Alternatively, commonly-known methods known as peptide synthesis methods ("Fundamentals and Experiments of Peptide Synthesis", Maruzen Co., Ltd., 1985) (this literature is incorporated herein by referenced)), or enzymatic peptide synthesis methods (e.g., WO2004/011653 (this literature is incorporated herein by reference)) can be also used. As valyl-glycine used in the present invention, a reaction solution containing valyl-glycine obtained by the above various methods may be used as it is, unless it hinders the reaction in the subsequent step. Alternatively, a solution containing purified valyl-glycine or an isolated crystal may be used.

The salt of valyl-glycine may be any chemically acceptable salt. Specific examples of the "chemically acceptable salt" for acidic groups such as carboxyl group may include ammonium salt, salts with alkali metals such as sodium and potassium, salts with alkaline earth metals such as calcium and magnesium, aluminum salt, zinc salt, salts with organic amines such as triethylamine, ethanolamine, morpholine, pyrrolidine, piperidine, piperazine, and dicyclohexylamine, and salts with basic amino acids such as arginine and lysine. Specific examples for basic groups may include salts with inorganic acids such as hydrochloric acid, sulfuric acid, phosphoric acid, nitric acid, and hydrobromic acid, salts with organic carboxylic acids such as acetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid, and malic acid, and salts with organic sulfonic acids such as methanesulfonic acid, benzenesulfonic acid, and p-toluenesulfonic acid.

The γ-glutamyl group donor can be selected from γ-glutamyl compounds. The γ-glutamyl group donor include, for example, glutamine, glutamic acid-γ-alkyl esters such as glutamic acid-γ-methyl ester, and salts thereof. Of these, glutamine or salts thereof are preferred. For the salts here, the "chemically acceptable salts" defined above can be used.

The reaction between valyl-glycine or a salt thereof and the γ-glutamyl group donor may be carried out in a batch method or column method. In the batch method, valyl-glycine or a salt thereof, a γ-glutamyl group donor, and γ-glutamyl transferase or a microorganism containing the enzyme may be mixed in a solvent in a reactor. The reaction may proceed with or without stirring. In the batch method, for example, a solution containing valyl-glycine or a salt thereof and a γ-glutamyl group donor is passed through a column packed with immobilized cells or immobilized enzymes.

The solvent used for the reaction between valyl-glycine or a salt thereof and a γ-glutamyl group donor in the presence of γ-glutamyl transferase or a microorganism containing the enzyme is not particularly limited as long as it enables enzymatic reactions, but preferably water and buffers. As the buffer, a phosphate buffer, citrate buffer, tris-hydrochloric acid buffer (tris(hydroxymethyl)aminomethane-hydrochloric acid buffer), acetic acid buffer, boric acid buffer, other buffers can be used. As the salt, the "chemically acceptable salt" defined above can be used. For the pH of the solvent to be used, the solvent may be a buffer, or the pH of the solvent may be appropriately adjusted with an acidic or alkaline pH adjuster. The pH ranges, for example, from 6.0 to 10.0, preferably from 6.5 to 9.0.

The reaction time or the flow rate of the solution can be appropriately set according to the concentration of the substrate, the amount of γ-glutamyl transferase with respect to the substrate, or other factors. Specifically, for example, the amount of the enzyme to be added can be determined on the basis of the value of the enzyme activity measured under certain conditions. For example, the enzyme activity can be measured by using an appropriate amount of enzyme and a solution containing 0.1 M glutamine, 0.1 M valyl-glycine, and 0.1 M potassium phosphate (pH 7.6) at a reaction temperature of 37° C. for a reaction time of 1 to 10 minutes. For example, when the amount of enzyme that can produce 1 mol of γ-glutamyl-valyl-glycine per minute in such conditions was defined as 1 U, the reaction can proceed with substrate concentrations of 1 to 2000 mM glutamine being a γ-glutamyl group donor and 1 to 2000 mM valyl-glycine as well as an enzyme concentration of 0.1 to 100 U/ml. The reaction temperature is usually from 15 to 50° C., preferably from 15 to 45° C., more preferably from 20 to 40° C.

Although the molar ratio of valyl-glycine or a salt thereof and the γ-glutamyl group donor in the solution before the reaction may depend on the type of the γ-glutamyl group donor used for the reaction, the molar ratio of valyl-glycine to γ-glutamyl group donor is usually preferably from 1:0.1 to 1:10. The concentration of Val-Gly and the γ-glutamyl group donor in the solution is each usually from 1 to 2000 mM, preferably from 100 to 2000 mM, more preferably from 100 to 1000 mM.

The amount of γ-glutamyl transferase or a salt thereof with respect to valyl-glycine used as the substrate is usually from 0.01 to 1000 U, preferably from 0.1 to 500 U, more preferably from 0.1 to 100 U per millimole of the substrate.

When γ-glutamyl transferase or a microorganism containing the enzyme is used, peptidase, particularly PepD, if contained, decomposes valyl-glycine or a salt thereof being the substrate and/or γ-glutamyl-valyl-glycine being the product. Therefore, a PepD-gene disrupted strain is preferably used as a microorganism. Alternatively, the peptidase activity can also be inhibited by adding to the reaction system a metal chelator, which chelates metal ions, e.g., $Co^{2+}$, $Mn^{2+}$, and $Fe^{2+}$, required for the enzyme activity of peptidases.

As described above, γ-glutamyl-valyl-glycine is generated in the reaction solution after the reaction starts, thereby providing a mixed solution containing valyl-glycine or a salt thereof and γ-glutamyl-valyl-glycine.

When the mixed solution containing valyl-glycine or the salt thereof and γ-glutamyl-valyl-glycine is an enzyme reaction solution obtained using the cells of the microorganism containing γ-glutamyl transferase, the mixed solution may be appropriately sterilized by heating in an autoclave, acid and alkali treatment, filtration, or others to prepare a sterile solution, or may be subjected to proper pH adjustment before the subsequent step, which are preferred in view of the design of the treatment process.

(2) Step of Adjusting Amount of Valyl-Glycine or Salt Thereof in Prepared Mixed Solution to 0.1 Mass % or More and Less than 20 Mass %

The amount of valyl-glycine or the salt thereof in the mixed solution of valyl-glycine or the salt thereof and γ-glutamyl-valyl-glycine is adjusted to, for example, 0.1 mass % or more and less than 20 mass %, preferably from 0.1 to 18 mass %, more preferably from 0.1 to 15 mass %, still more preferably from 1 to 10 mass % based on the free form relative to the mass of the γ-glutamyl-valyl-glycine in the mixed solution. Such adjustment can prevent gelation of the γ-glutamyl-valyl-glycine solution and can also increase the yield of the γ-glutamyl-valyl-glycine crystal in the subsequent crystallization process to form the γ-glutamyl-valyl-glycine crystal. The γ-glutamyl-valyl-glycine crystal formed after adjusting the amount of valyl-glycine or the salt thereof in this range is preferred because of its desired crystal size.

The process of adjusting the amount of valyl-glycine or the salt thereof include, for example, a process in which γ-glutamyl-valyl-glycine in the mixed solution is adsorbed to an adsorption resin, and valyl-glycine or the salt thereof in the mixed solution is allowed to flow through the adsorption resin; and a process using a membrane which valyl-glycine permeates but γ-glutamyl-valyl-glycine fails to permeate. Specifically, the amount of valyl-glycine or the salt thereof may be adjusted by separating valyl-glycine or the salt thereof from γ-glutamyl-valyl-glycine according to any of the following processes.

1. Process based on the difference in hydrophobic and hydrophilic interaction
2. Process based on the difference in isoelectric point
3. Process based on the difference in molecular weight Process 1 based on the difference in hydrophobic and hydrophilic interaction takes advantage of higher hydrophobicity of γ-glutamyl-valyl-glycine than that of valyl-glycine. Specifically, for example, an acid (e.g., hydrochloric acid or sulfuric acid) or alkali (e.g., sodium hydroxide) is added to the mixed solution containing valyl-glycine or the salt thereof and γ-glutamyl-valyl-glycine to adjust the pH to 3.0. Subsequently, the mixed solution is passed through a synthetic adsorption resin at a flow rate that causes no decomposition of γ-glutamyl-valyl-glycine at a room temperature (25° C.) to adsorb γ-glutamyl-valyl-glycine to the resin while valyl-glycine or the salt thereof is allowed to flow through the resin. After the mixed solution is passed through, water in a volume that is one to two times the column volume is passed through the resin to wash away unadsorbed valyl-glycine or salt thereof remaining in the resin, and then adsorbed γ-glutamyl-valyl-glycine is eluted with, for example, to 30 vol % of a methanol solution.

As the synthetic adsorption resin, for example, SP-207 (produced by Mitsubishi Chemical Corporation) can be used. Process 2 based on the difference in isoelectric point is a process of separating γ-glutamyl-valyl-glycine and valyl-glycine by adsorbing γ-glutamyl-valyl-glycine and valyl-glycine to an adsorption resin, such as strong cation exchange resins, followed by gradual elution using an alkali eluent. Specifically, for example, an acid (e.g., hydrochloric acid or sulfuric acid) or alkali (e.g., sodium hydroxide) is added to the mixed solution containing valyl-glycine or the salt thereof and γ-glutamyl-valyl-glycine to adjust the pH to 2.0. Subsequently, the mixed solution is passed through an ion exchange resin at a flow rate that causes no decomposition of γ-glutamyl-valyl-glycine at a room temperature (25° C.) to adsorb γ-glutamyl-valyl-glycine to the resin while valyl-glycine or the salt thereof is allowed to flow through the resin. After the mixed solution is passed through, water in a volume approximately equivalent to the column volume is passed through the resin to wash away unadsorbed components remaining in the ion exchange resin. Subsequently, adsorbed valyl-glycine or salt thereof and γ-glutamyl-valyl-glycine are eluted with a 0.1 to 0.25 N sodium hydroxide aqueous solution. This allows first elution of γ-glutamyl-valyl-glycine and subsequent elution of valyl-glycine or the salt thereof. The temperature increase to about 50 to 60° C. during the elution is preferred because of improved resolution of these.

The adsorption resin to be used here is preferably an ion exchange resin, more preferably a strong cation exchange resin, for example, UBK-550 (produced by Mitsubishi Chemical Corporation) and UBK-555 (produced by Mitsubishi Chemical Corporation).

Process 3 based on the difference in molecular weight is a process of separating valyl-glycine and γ-glutamyl-valyl-glycine using a nano-filtration (NF) membrane which valyl-glycine permeates but γ-glutamyl-valyl-glycine fails to (or hardly) permeate(s).

(3) Step of Subjecting γ-Glutamyl-Valyl-Glycine Solution to Crystallization Procedure to Produce γ-Glutamyl-Valyl-Glycine Crystal As the method for forming a γ-glutamyl-valyl-glycine crystal from the γ-glutamyl-valyl-glycine solution in which the amount of the valyl-glycine or the salt thereof has been adjusted, an ordinary crystallization procedure and recrystallization process can be used. The crystallization procedure include, for example, crystallization by a cooling method, crystallization by a poor solvent method, crystallization by a suspension method, crystallization by a neutralization method, and crystallization by a concentration method. Any crystallization procedure may be carried out as long as it is the step of dissolving or suspending the target γ-glutamyl-valyl-glycine in a crystallization solvent to undergo crystallization. Cooling crystallization and poor solvent crystallization may be combined.

The crystallization solvent may be any solvent commonly known as a crystallization solvent that can be used, and a single solvent or mixed solvent may be used.

As the mixed solvent, a mixed solvent obtained by mixing a proper amount of solvent (good solvent) dissolving the target compound (γ-glutamyl-valyl-glycine) well and a proper amount of solvent (poor solvent) soluble in this good solvent but hardly dissolving the target compound can be used. The good solvent may contain two or more solvents while the poor solvent may contain two or more solvents. In this case, it is preferred that these solvents be uniformly mixed with each other.

It is also preferred that a crystallization solution be obtained by adding a poor solvent to the solution (aqueous solution) obtained in the previous step of preparing the γ-glutamyl-valyl-glycine solution.

Poor solvents include alcohols (e.g., methanol, ethanol, octanol), ethers (e.g., diethyl ether), acetate esters (e.g., ethyl acetate), hydrocarbons (e.g., toluene, cyclohexane, hexane), and mixed solutions of these and water. Of these, alcohols are preferred.

Specifically, for example, the following crystallization method is mentioned.

That is, first, methanol, ethanol, or another solvent is optionally added to the γ-glutamyl-valyl-glycine solution in which the amount of valyl-glycine or the salt thereof has been adjusted, and the solution is cooled to, for example, from 0 to 15° C., preferably from 5 to 10° C. to precipitate crystals. The precipitated crystals are separated from the solution, and washed with, for example, methanol, ethanol, or another solvent to give wet crystals. The wet crystals are dried at, for example, from 30 to 100° C., preferably from 40 to 50° C. under ordinary pressure or reduced pressure to give dried crystals.

[2] γ-Glutamyl-Valyl-Glycine Crystal

The present invention may also relate to a γ-glutamyl-valyl-glycine crystal produced by the method as described above.

The γ-glutamyl-valyl-glycine crystal produced by the method of the present invention is formed through the enzyme reaction using valyl-glycine as a material and may contain, as impurities, by-products characteristic of the enzyme reaction, such as valyl-valine and valyl-valyl-glycine. The concentration of the impurities is also significantly reduced in the crystal obtained by relatively increasing the crystallization yield. In the present invention, the total concentration of one or more impurities selected from valyl-valine, salts of valyl-valine, valyl-valyl-glycine, and salts of valyl-valyl-glycine in the crystal is usually 2.0 mass % or less, preferably 1.2 mass % or less. The lower limit of the total concentration of the impurities is not particularly limited, but may be usually 0.01 mass % or more, preferably 0.02 mass % or more, more preferably 0.1 mass % or more. The total concentration of the impurities is in the range of preferably from 0.02 to 2.0 mass %, more preferably from 0.02 to 1.2 mass %.

The γ-glutamyl-valyl-glycine crystal produced by the method of the present invention may contain as an impurity valyl-glycine being a material, but the concentration of valyl-glycine is also significantly reduced in the crystal obtained by relatively increasing the crystallization yield. In the present invention, the concentration of valyl-glycine in the crystal is, for example, 3.0 mass % or less, preferably 2.2 mass % or less. The lower limit of the concentration is not particularly limited, and the valyl-glycine concentration is preferably 0%, but may be usually 0.01 mass % or more, more typically 0.1% mass or more (may be in the range of from detection limit to 2.2 mass %, i.e., in the range of from 0 to 2.2 mass %).

The γ-glutamyl-valyl-glycine crystal produced by the method of the present invention is larger than γ-glutamyl-valyl-glycine crystals usually obtained by the enzyme reaction and particularly has a characteristic of a large transverse diameter (or thickness) because the crystal is formed after reducing the amount of valyl-glycine or the salt thereof.

Specifically, the present invention provides novel γ-glutamyl-valyl-glycine crystals wherein the total content of at least one selected from valyl-valine, salts of valyl-valine, valyl-valyl-glycine, and salts of valyl-valyl-glycine in the crystals is from 0.02 to 1.2 mass %, wherein the crystals are crystals whose entire images are included in the region of 415 µm×332 µm in the image of the crystals taken with an optical microscope, wherein the crystals having a longitudinal length of 35 µm or more have a mean of the transverse diameter of 2.1 µm or more, more typically 2.3 µm or more, although the upper limit is not particularly limited, usually 4.0 µm or less, more typically 3.5 µm or less, preferably from 2.1 to 4.0 µm, more preferably from 2.3 to 3.5 µm. Furthermore, novel γ-glutamyl-valyl-glycine crystals are provided wherein the concentration of valyl-glycine in the above crystals is 2.2 mass % or less.

The mean of the transverse diameter of the crystal in the present invention can be determined in the following manner. That is, a small amount of slurry before crystal separation is taken out, and the crystal size of crystals in the slurry is measured with, for example, an optical microscope as described below.

Produced by Olympus Corporation

Optical microscope BX61

Object lens UPlan-FI 20×/0.5

Ocular lens WH10×/22

Analysis software CellSens Standard 1.6

The images of crystals taken with the above optical microscope and lens are saved as image files (for example, TIF files) by the above analysis software. For focused crystals whose entire images are included in the region of 415 µm×332 µm in the image, the longitudinal length (maximum diameter) and the transverse diameter (minimum diameter) are measured by encircling each crystal in the "rotated square" mode with the function "measurement" of the analysis software. In the obtained data, the transverse diameter data of crystals having a longitudinal length of 35 µm or more are extracted to obtain the mean of the transverse diameter.

The present invention will be described below in more detail by way of Examples, but these Examples do not limit the present invention.

EXAMPLES

[1] Method for Producing γ-Glutamyl-Valyl-Glycine Crystal

The γ-glutamyl-valyl-glycine crystal is produced by the following steps:

(1) preparing a mixed solution of valyl-glycine or a salt thereof and γ-glutamyl-valyl-glycine;

(2) adjusting the amount of valyl-glycine or the salt thereof in the prepared mixed solution to 0.1 mass % or more and less than 20 mass %; and (3) subjecting the γ-glutamyl-valyl-glycine solution to a crystallization procedure to produce a γ-glutamyl-valyl-glycine crystal, as described above.

(1) Step of Preparing Mixed Solution of Valyl-Glycine or Salt Thereof and γ-Glutamyl-Valyl-Glycine γ-Glutamyl transferase (GGT) and *Escherichia coli* (*E. coli*) transformed with a GGT expression plasmid that were obtained as described below were used as γ-glutamyl transferase or a microorganism containing the enzyme in the present invention.

Test Example 1

Construction of GGT Expression Plasmid

A γ-glutamyl transferase (GGT) expression plasmid was constructed by inserting the ggt gene of *Escherichia coli* into an expression plasmid pSF12_Sm_Aet containing the rpoH promoter described below.

First, in order to delete the NdeI recognition site (restriction site derived from pUC18) in the pUC18-derived plasmid pSF_Sm_Aet containing a peptide-producing enzyme gene derived from the *Sphingobacterium* sp. FERM BP-8124 and the phoC promoter (WO2006/075486A1), PCR was performed using pSF_Sm_Aet as a template and the primers having the sequences of SEQ ID NOS: 5 and 6 with "Quik Change Site-Directed Mutagenesis Kit" produced by Stratagene Corp. according to the manufacturer's protocol. The obtained PCR product was digested with DpnI, and then the *Escherichia coli* JM109 strain was transformed with the reaction solution, applied to a LB-agar medium containing 100 mg/L of ampicillin sodium (Amp), and cultured at 25° C. for 36 hours. Plasmids were extracted from grown colonies of the transformants according to a known method, and the nucleotide sequences thereof were determined with 3100 Genetic Analyzer (produced by Applied Biosystems). The plasmid having the target structure was designated as pSF1_Sm_Aet. The FERM BP-8124 strain was designated as AJ110003, and deposited with International Patent Organism Depository, National Institute of Advanced Industrial Science and Technology (Tsukuba Central 6, 1-1-1, Higashi, Tsukuba, Ibaraki, 305-8566, Japan), under Accession No. FERM BP-8124 as of Jul. 22, 2002, under the Budapest Treaty.

Next, in order to introduce the NdeI recognition sequence into the start methionine site of the peptide-producing enzyme gene derived from *Sphingobacterium* sp. FERM BP-8124 in pSF1_Sm_Aet, PCR was performed using pSF1_Sm_Aet as a template and the primers having the sequences of SEQ ID NOS: 7 and 8 with "Quik Change Site-Directed Mutagenesis Kit" mentioned above. The obtained PCR product was digested with DpnI, and then the *Escherichia coli* JM109 strain was transformed with the reaction solution, applied to a LB-agar medium containing 100 mg/L of Amp, and cultured at 25° C. for 24 hours. Plasmids were extracted from grown colonies of the transformants according to a known method, and the nucleotide sequences thereof were determined with 3100 Genetic Analyzer (produced by Applied Biosystems). The plasmid having the target structure was designated as pSF2_Sm_Aet.

Next, the phoC promoter of pSF2_Sm_Aet was replaced with the rpoH promoter according to the following method. The rpoH promoter region was obtained from the chromosomal DNA of the *Escherichia coli* W3110 strain by PCR. PCR was performed using the chromosomal DNA of the W3110 strain as a template, the primer having the sequence of SEQ ID NO: 9 (in which a nucleotide sequence including the XbaI recognition sequence is added to the 5' end of the rpoH promoter region) as a sense primer, the primer having the sequence of SEQ ID NO: 10 (in which a nucleotide sequence including the NdeI recognition sequence is added to the 5' end of the nucleotide sequence complementary to the rpoH promoter region) as an antisense primer, and KOD-plus- (Toyobo Co., Ltd.) as a polymerase, with 30 cycles of the conditions of 94° C. for 30 seconds, 52° C. for 1 minute, and 68° C. for 30 seconds according to the manufacturer's protocol.

Next, the obtained PCR product was digested with XbaI/NdeI, and then subjected to agarose gel electrophoresis to excise the target DNA of about 0.4 kb. The DNA was ligated to the pSF2_Sm_Aet fragment (about 4.7 kb) digested with XbaI/NdeI by using DNA Ligation Kit Ver. 2.1 (produced by Takara Bio Inc.). The *Escherichia coli* JM109 strain was transformed with the reaction solution, applied to a LB-agar medium containing 100 mg/L of Amp, and cultured at 25° C. for 36 hours. Plasmids were extracted from grown colonies of the transformants according to a known method, and the nucleotide sequences thereof were determined with 3100 Genetic Analyzer (produced by Applied Biosystems). The plasmid having the target structure was designated as pSF12_Sm_Aet.

The ggt gene of *Escherichia coli* was obtained from the chromosomal DNA of the *Escherichia coli* W3110 strain by PCR. PCR was performed using the chromosomal DNA of the W3110 strain as a template, the primer having the sequence of SEQ ID NO: 11 (in which a nucleotide sequence including the NdeI recognition sequence is added to the 5' end of the region containing the initiation codon of the ggt gene) as a sense primer, the primer having the sequence of SEQ ID NO: 12 (in which a nucleotide sequence including the PstI sequence is added to the 5' end of the nucleotide sequence complementary to the sequence including the termination codon of the ggt gene) as an antisense primer, and KOD-plus- with 30 cycles of the conditions of 94° C. for 30 seconds, 52° C. for 1 minute, and 68° C. for 120 seconds according to the manufacturer's protocol. Next, the obtained PCR product was digested with NdeI/PstI, and then subjected to agarose gel electrophoresis to excise the target DNA of about 1.8 kb. The DNA was ligated to the pSF2_Sm_Aet fragment (about 3.0 kb) digested with NdeI/PstI by using DNA Ligation Kit Ver. 2.1 (produced by Takara Bio Inc.). The *Escherichia coli* JM109 strain was transformed with the reaction solution, applied to a LB-agar medium containing 100 mg/L of Amp, and cultured at 25° C. for 36 hours. Plasmids were extracted from grown colonies of the transformants according to a known method, and the nucleotide sequences thereof were determined with 3100 Genetic Analyzer (produced by Applied Biosystems). The obtained plasmid was a GGT expression plasmid having the target structure and designated as pSF12_ggt.

Test Example 2

Preparation of pepD-Gene Disrupted Strain (Host Strain) Derived from *Escherichia Coli* JM 109 Strain A PepD non-producing strain was constructed with the *Escherichia coli* JM 109 strain as a parent strain. PepD is encoded by the pepD gene (GenBank Accession: 7438954, SEQ ID NO: 3).

Each gene was disrupted by a combined method (see WO2005/010175 (this literature is incorporated herein by reference)) of the method called "Red-driven integration", first developed by Datsenko and Wanner (Proc. Natl. Acad. Sci. USA, vol. 97, No. 12, pp. 6640-6645, 2000) and an excision system derived from λ phage (Cho E H, Gumport R I, and Gardner J F, J. Bacteriol., 184 (18): 5200-3, 2002 September, Interactions between integrase and excisionase in the phage lambda excisive nucleoprotein complex (this literature is incorporated herein by reference)). According to the "Red-driven integration" method, a gene-disrupted strain can be constructed in one step by using a PCR product obtained with as a primer a synthetic oligonucleotide designed to have a part of the target gene at the 5' side and a part of an antibiotic resistance gene at the 3' side. By further using the excision system derived from λ phage in combination, the antibiotic resistance gene incorporated into the gene-disrupted strain can be removed.

The plasmid pMW118-attL-Cm-attR was used as a template in PCR. pMW118-attL-Cm-attR (WO 2006/078039) is a plasmid in which the attL and attR genes, being the attachment sites of λ phage, and the cat gene, being an antibiotic resistance gene, are inserted into pMW118 (produced by Nippon Gene Co., Ltd.) with these genes being inserted in the order of attL-cat-attR. PCR was performed using as primers synthetic oligonucleotides having the sequences corresponding to the both ends of these attL and attR at the 3' ends and the sequence corresponding to a part of the target gene pepD gene at the 5' end.

A DNA fragment for pepD-gene disruption was prepared by PCR using the primers having the sequences of SEQ ID NOS: 13 and 14 and KOD-plus- with 30 cycles of the conditions of 94° C. for 30 seconds, 52° C. for 1 minute, and 68° C. for 120 seconds according to the manufacturer's protocol.

The DNA fragments for gene disruption obtained as described above were each purified by agarose gel electrophoresis and introduced by electroporation into the *Escherichia coli* JM109 strain containing the plasmid pKD46 having a temperature sensitive replication ability. The plasmid pKD46 (Proc. Natl. Acad. Sci. USA, vol. 97, No. 12, p. 6640-45, 2000) includes a phage λ DNA fragment of total 2,154 nucleotides (GenBank/EMBL Accession: J02459, Positions 31088 to 33241) including the genes (γ, β, exo genes) encoding Red recombinase of the λ Red homologous recombination system under the control of the arabinose-inducible $P_{araB}$ promoter. The plasmid pKD46 is necessary for incorporating the DNA fragment for gene disruption into the chromosome of the JM109 strain. Competent cells for electroporation were prepared in the following manner. That is, the *Escherichia coli* JM109 strain containing the plasmid pKD46 was cultured at 30° C. for 20 hours in a LB medium containing 100 mg/L of Amp, and the culture medium was diluted 50 times with 2 ml of a SOB medium (Molecular Cloning A Laboratory Manual, 2nd edition, Sambrook, J. et al., Cold Spring Harbor Laboratory Press (1989) (this literature is incorporated herein by reference)) containing Amp (100 mg/L). Cells in the obtained dilution were grown at 30° C. to obtain an OD600 of about 0.3, and then 70 μl of 10% (v/v) L-arabinose was added to the dilution, which was then cultured at 37° C. for one hour. The obtained culture medium was concentrated 65 times, and the cells were washed three times with 10% (v/v) glycerol to be ready for use in electroporation. Electroporation was performed using 30 μl of competent cells and about 100 ng of the PCR product.

After the electroporation, 0.27 mL of a SOC medium (Molecular Cloning: A Laboratory Manual, 2nd edition, Sambrook, J. et al., Cold Spring Harbor Laboratory Press (1989) (this literature is incorporated herein by reference)) was added to the cell suspension and the cells were cultured at 37° C. for 3 hours. The cells were then cultured on a LB-agar medium containing chloramphenicol (Cm, 50 mg/L) at 37° C. to select Cm resistant recombinants. Next, in order to remove the pKD46 plasmid, the recombinants were cultured on a LB-agar medium containing Cm (50 mg/L) at 42° C., and the obtained colonies were examined for the Amp resistance to obtain an Amp sensitive strain from which pKD46 had been removed. Disruption of the pepD gene of the mutants identified with the Cm resistant gene was confirmed by PCR. The obtained pepD-gene disrupted strain was designated as a JM109ΔpepD:att-cat strain.

Next, in order to remove the att-cat gene introduced into the pepD gene, pMW-intxis-ts was used as a helper plasmid. pMW-intxis-ts was a plasmid carrying the gene encoding integrase (Int) of phage λ and the gene encoding excisionase (Xis) and having a temperature sensitive replication ability. When pMW-intxis-ts is introduced into cells, pMW-intxis-ts recognizes attL or attR on the chromosome to cause recombination and thus to excise the gene between attL and attR, which results in that only the attB sequence remains on the chromosome. Competent cells of the JM109ΔpepD:att-cat strain obtained above were prepared according to a conventional method, transformed with pMW-intxis-ts, and cultured on a LB-agar medium containing 100 mg/L of Amp at 30° C. to select Amp resistant strains.

Next, in order to remove the pMW-intxis-ts plasmid, the transformants were cultured on the LB-agar medium at 42° C., and the obtained colonies were examined for the Amp resistance and Cm resistance to obtain a Cm and Amp sensitive strain in which att-cat and pMW-intxis-ts had been removed and the pepD gene had been disrupted. This strain is a host strain of *Escherichia coli* (*E. coli*) used in subsequent transformation with the GGT expression plasmid, and designated as a JM109ΔpepD strain.

Test Example 3

Preparation of Cultured Cells (B101 Strain) of ggt-Gene-Enhanced Strain of *Escherichia Coli*

The JJM109ΔpepD strain obtained in Test Example 2 was transformed with pSF12_ggt, which was the GGT expression plasmid obtained by Test Example 1, and designated as a B101 strain. The B101 strain was cultured at 25° C. for 16 hours using a LB medium[1.0% (w/v) peptone, 0.5% (w/v) yeast extract, and 1.0% (w/v) NaCl] containing 100 mg/L of Amp. The B101 strain in the above obtained culture medium was subcultured in 50 ml of a TB medium [Terrific Broth, Molecular Cloning A Laboratory Manual, 3rd edition, Sambrook, J. et al., Cold Spring Harbor Laboratory Press (2001) (this literature is incorporated herein by reference)] containing 100 mg/L of Amp at 25° C. for 24 hours using a 500-ml Sakaguchi flask so that the inoculum dose was 1.0% (v/v).

The obtained culture medium was centrifuged (8,000×g, 10 minutes, 4° C.) to collect wet cells as precipitates. Obtained were 3.5 g of wet cells per 100 ml of the culture medium. The wet cells were washed with a 0.85% (w/v) NaCl aqueous solution, and a suspension (suspension I) was prepared to contain 35 mg/ml of the cells.

The obtained suspension I was used as cells (B101 strain) of *Escherichia coli* (*E. coli*) transformed with the GGT expression plasmid.

Test Example 4

Evaluation of GGT Enzyme Activity of Cells (B101 Strain)

The GGT enzyme activity was determined with suspension I as an enzyme source. As an enzyme activity measurement method, a hydrolysis activity measurement method with γ-glutamyl-p-nitroanilide as a substrate [Suzuki H., et al., γ-Glutamyltranspeptidase from *Escherichia coli* K-12: Purification and Properties, J. Bacteriol. 168(3): 1325-1331, 1986 December (this literature is incorporated herein by reference)] was used. The reaction solution contained 2.5 mM γ-glutamyl-p-nitroanilide, 50 mM tris-hydrochloric acid buffer (trishydroxymethylaminomethane-hydrochloric acid buffer) (pH 8.73), and diluted suspension I. The reaction volume was 0.5 ml and after the reaction at 37° C. for 10 minutes, 1 ml of a 3.5 N acetic acid solution was added to terminate the reaction. The centrifugation (10,000×g, 5 minutes, 4° C.) was performed to remove insoluble materials. The difference in optical absorbance at 405 nm between the supernatant of diluted suspension I and that of a blank (0.85% (w/v) NaCl aqueous solution was used instead of diluted suspension I) was measured to determine the amount of produced p-nitroaniline ($\epsilon_{405nm}$=9920 $M^{-1}cm^{-1}$). When the amount of enzyme that can produce 1 mol of p-nitroaniline per minute in such conditions was defined as 1 U, the enzyme activity of suspension I was 2.6 U/ml.

Test Example 5

Preparation of GGT Crude Enzyme Solution Containing GGT

A periplasm fraction in which GGT was localized was produced from the cells (B101 strain) obtained in Test Example 3 to prepare a GGT crude enzyme solution containing GGT. The solution was prepared according to modification of the method described in the literature [Suzuki H., et al., γ-Glutamyltranspeptidase from *Escherichia coli* K-12: Formation and Localization, J. Bacteriol. 168(3): 1332-1335, 1986 December (this literature is incorporated herein by reference)].

Specifically, 1.2 g of wet cells were first uniformly dispersed in 15 ml of a solution containing 0.2 M tris-hydrochloric acid buffer (pH 7.5), 20% (w/v) sucrose, 1 mM EDTA, and 30 U/ml lysozyme, and the dispersion was shaken gently at 25° C. for 10 minutes. Ice-cooled pure water (15 ml) was added to the dispersion, followed by inversion mixing. The dispersion was then cooled in ice water for 10 minutes. The supernatant obtained by centrifugation (8,000×g, 15 minutes, 4° C.) was dialyzed against 0.1 M potassium phosphate buffer (pH 7.0) to provide a periplasm fraction. This periplasm fraction, which contained 14 mg of a GGT-containing protein, was given as a GGT crude enzyme solution containing GGT. When the GGT enzyme activity of this enzyme solution was determined by the same method as in Test Example 4, the GGT enzyme activity was 0.45 U/mg.

Example 1

Synthesis of γ-Glutamyl-Valyl-Glycine Using GGT Crude Enzyme Solution of Test Example 5

The enzyme reaction was carried out using the GGT crude enzyme solution obtained in Test Example 5 and L-glutamine and Val-Gly as substrates to produce γ-glutamyl-valyl-glycine.

Specifically, 0.2 M L-glutamine, 0.2 M valyl-glycine, 0.1 M potassium phosphate buffer (pH 7.0), and the periplasm fraction (GGT crude enzyme solution) obtained in Test Example and having a protein concentration of 1.2 mg/ml were mixed to prepare a solution. The pH of the solution was adjusted by optionally adding a KOH aqueous solution when the reaction started. The reaction proceeded at a reaction temperature of 37° C. for a reaction time of one hour. The amount of valyl-glycine and γ-glutamyl-valyl-glycine was determined by HPLC after completion of the reaction. As the column for the HPLC, Synergi 4μ Hydro-RP 80A produced by Phenomenex (particle size: 4 μm, inner diameter: 4.6 mm, length: 250 mm) was used. As the eluent for the HPLC, solution A (50 mM sodium dihydrogen phosphate (pH 2.5, the pH was adjusted with phosphoric acid) and solution B (1:1 mixture of solution A and acetonitrile) were used. The column temperature was 40° C., and the UV detection wavelength was 210 nm. The gradient of the eluent was 0% to 5% solution B from 0 to 5 minutes, 5% solution B from 5 to 15 minutes, 5% to 80% solution B from 15 to 30 minutes, 80% to 0% solution B from 30 to 30.1 minutes, and 0% solution B from 30.1 to 50 minutes. The results of the measurement by HPLC indicated that the mixed solution obtained by the reaction contained 25.8 mM γ-glutamyl-valyl-glycine and 171.0 mM valyl-glycine (valyl-glycine to γ-glutamyl-valyl-glycine in the mixed solution: 381 mass %).

Example 2

Synthesis of γ-Glutamyl-Valyl-Glycine Using Cells (B101 Strain)

The enzyme reaction was carried out using the cells (B101 strain) obtained in Test Example 3, and as substrates valyl-glycine and L-glutamine being a γ-glutamyl group donor to produce γ-glutamyl-valyl-glycine.

Specifically, 0.2 M L-glutamine, 0.2 M valyl-glycine, 0.1 M potassium phosphate buffer, and suspension I containing the cells (B101 strain) in the amount indicated in Table 1 below were mixed to provide a solution.

The pH of the solution was adjusted with potassium phosphate buffer and optionally a KOH aqueous solution. The pH when the reaction started was adjusted to 7.0 or 8.0. The solution was mixed under stirring to undergo the reaction at a reaction temperature of 37° C. for a reaction time of one hour. After completion of the reaction, the amount of valyl-glycine and γ-glutamyl-valyl-glycine was determined by the HPLC described in Example 1. The results are shown in Table 1. In Table below, valyl-glycine and γ-glutamyl-valyl-glycine were abbreviated as VG and EVG, respectively.

TABLE 1

| Wet cells | pH 7.0 when reaction started | | | pH 8.0 when reaction started | | |
|---|---|---|---|---|---|---|
| added (mg/ml) | VG (mM) | EVG (mM) | VG/EVG (wt %) | VG (mM) | EVG (mM) | VG/EVG (wt %) |
| 8.8 | 186.2 | 13.1 | 816% | 145.0 | 48.5 | 172% |
| 17.6 | 172.5 | 24.6 | 403% | 127.2 | 60.6 | 121% |
| 35.2 | 169.5 | 26.5 | 367% | 151.2 | 36.6 | 237% |
| 52.8 | 171.5 | 21.9 | 450% | 167.4 | 21.2 | 453% |

Example 3

Synthesis of γ-Glutamyl-Valyl-Glycine Using Cells (B101 Strain)

The enzyme reaction was carried out using the cells (B101 strain) obtained in Test Example 3, and as substrates valyl-glycine and L-glutamine being a γ-glutamyl group donor to produce γ-glutamyl-valyl-glycine.

Specifically, 0.2 M valyl-glycine, 0.1 M potassium phosphate buffer, and suspension I containing 17.6 mg of the wet cells (B101 strain) were mixed to provide a solution. The amount of L-glutamine was from 1.0 to 3.0 equivalents to valyl-glycine. The pH of the solution was adjusted with pH 8.0 potassium phosphate buffer and optionally a KOH aqueous solution. The pH when the reaction started was adjusted to 8.0. The solution was mixed under stirring to undergo the reaction at a reaction temperature of 37° C. for a reaction time of one hour. After completion of the reaction, the amount of valyl-glycine and γ-glutamyl-valyl-glycine was determined by the HPLC described in Example 1. The results are shown in Table 2.

TABLE 2

| L-glutamine equivalent | VG (mM) | EVG (mM) | VG/EVG (wt %) |
|---|---|---|---|
| 1.0 | 135.5 | 69.8 | 111% |
| 1.5 | 113.2 | 84.3 | 77% |
| 2.0 | 112.4 | 89.9 | 72% |
| 2.5 | 109.5 | 89.3 | 70% |
| 3.0 | 107.8 | 89.1 | 69% |

As shown in the results of Examples 1 to 3, valyl-glycine was converted into a γ-glutamyl compound by using GGT or cells capable of producing GGT to provide γ-glutamyl-valyl-glycine.

(2) Step of Adjusting Amount of Valyl-Glycine or Salt Thereof in Prepared Mixed Solution to 0.1 Mass % or More and Less than 20 Mass %

The amount of valyl-glycine or the salt thereof in γ-glutamyl-valyl-glycine solution as obtained by the GGT enzyme reactions described in Examples 1 to 3 above was adjusted in the following manner.

Example 4

Adjustment of Valyl-Glycine Amount

A γ-glutamyl-valyl-glycine solution containing valyl-glycine obtained by the GGT enzyme reaction was heated at 121° C. for 20 minutes in an autoclave. Cells contained in the solution were then filtered through a 0.45-μm microfilter membrane (produced by Advantec Co., Ltd.) to provide 209.08 g of a sterile solution containing 15.89 g (52.39 mmol) of γ-glutamyl-valyl-glycine and 6.09 g (34.99 mmol) of valyl-glycine. Furthermore, the sterile solution was adjusted to pH 3.0 with 35% HCl (mass ratio of valyl-glycine to γ-glutamyl-valyl-glycine in the solution=38.4 mass %). The pH-adjusted solution was passed through a column, 5 cm in inner diameter, packed with 650 mL of a synthetic adsorption resin (SP207 produced by Mitsubishi Chemical Corporation) at a flow rate of SV1 (650 mL/hr), and then 1300 mL of deionized water was passed through the column at this flow rate. After that, 1950 mL of 10% MeOH and 1950 mL of 20% MeOH were passed through the column at a flow rate of SV2 (1300 mL/hr). Of the eluent, a fraction from 1.8 to 5.8 RV (1170 to 3770 mL) were collected to obtain 2513.63 g of a recovery solution containing 15.07 g (49.69 mmol) of γ-glutamyl-valyl-glycine and 0.06 g (0.33 mmol) of valyl-glycine. The mass ratio of valyl-glycine to γ-glutamyl-valyl-glycine in the recovery solution was 0.4 mass %. Therefore, the mass ratio of valyl-glycine to γ-glutamyl-valyl-glycine in the γ-glutamyl-valyl-glycine solution was adjusted from 38.4 mass % to 0.4 mass % by Example 4.

(3) Step of Subjecting γ-Glutamyl-Valyl-Glycine Solution to Crystallization Procedure to Produce γ-Glutamyl-Valyl-Glycine Crystal Example 5

Preparation of γ-Glutamyl-Valyl-Glycine Crystal

The recovery solution (2513.63 g) obtained in Example 4, in which the amount of valyl-glycine had been adjusted, was concentrated to 99.03 g under reduced pressure and then 237 mL of MeOH was added to the solution over one hour while it was kept at 50° C. In the middle of the addition, 144 mg of seed crystals (γ-glutamyl-valyl-glycine crystal, prepared as described in Example of Patent Literature 1, the same applies hereinafter) were added to the solution at the time when 50 mL of MeOH was added. The entire solution was then cooled to 10° C. at 5° C./hr to precipitate crystals. The solution containing the precipitated crystals was further kept at 10° C. for 76.5 hours, and the precipitated crystals were separated to obtain unwashed wet crystals. The obtained unwashed wet crystals were washed with 40 mL of MeOH to provide 29.67 g of wet crystals. The wet crystals were dried under reduced pressure in a 40° C. condition to provide 11.05 g of dried crystals. The obtained crystals contained 10.77 g (35.52 mmol) of γ-glutamyl-valyl-glycine crystals (crystallization yield: 71.5 mass %).

It was confirmed that the yield was higher than Comparative Example 1 below with no step of adjusting the amount of valyl-glycine.

Comparative Example 1

Preparation of γ-Glutamyl-Valyl-Glycine Crystal

A γ-glutamyl-valyl-glycine solution containing valyl-glycine obtained by the GGT enzyme reaction was heated at 121° C. for 20 minutes in an autoclave. Cells contained in the solution were then filtered through a 0.45-μm microfilter membrane (produced by Advantec Co., Ltd.) to provide 100.11 g of a sterile solution containing 1.26 g (4.14 mmol) of γ-glutamyl-valyl-glycine and 0.26 g (1.48 mmol) of valyl-glycine. Furthermore, the sterile solution was adjusted to pH 3.0 with 35% HCl (mass ratio of valyl-glycine to γ-glutamyl-valyl-glycine in the solution=21 mass %). The pH-adjusted solution was concentrated to 8.24 g under reduced pressure and then 16.4 mL of MeOH was added to the solution over one hour while it was kept at 50° C. In the middle of the addition, 17.7 mg of seed crystals were added. The entire solution was then cooled to 10° C. at 5° C./hr to precipitate crystals. After the solution containing the precipitated crystals was further kept at 10° C. for 48 hours, the precipitated crystals were separated to obtain unwashed wet crystals. The obtained unwashed wet crystals were washed with 1.7 mL of MeOH to provide 1.44 g of wet crystals. The obtained crystals contained 0.54 g (1.77 mmol) of γ-glutamyl-valyl-glycine crystals and 0.001 g (0.003 mmol) of valyl-glycine (crystallization yield: 42.8 mass %).

Example 6

Preparation of γ-Glutamyl-Valyl-Glycine Crystal

Pure water (28.9 mL) was added to 9.98 g (32.89 mmol) of γ-glutamyl-valyl-glycine and 1.14 g (6.57 mmol) of valyl-glycine, and these components were dissolved in pure water at 75° C. to provide a solution (mass ratio of valyl-glycine to γ-glutamyl-valyl-glycine in the solution=11 mass %). The obtained solution was cooled to 50° C. at 10° C./hr. About 50 mg of seed crystals were added to the solution at 60° C. in the middle of the addition. The solution was kept at 50° C. for one hour after the temperature thereof reached 50° C., and 44 mL of MeOH was added to the solution over one hour. The solution was then cooled to 10° C. at 5° C./hr to precipitate crystals. After the solution containing the precipitated crystals was further kept at 10° C. for 30 hours or more, the precipitated crystals were separated to obtain unwashed wet crystals. The obtained unwashed wet crystals were washed with 26 mL of 90% MeOH to provide 11.41 g of wet crystals. The wet crystals were dried under reduced pressure in a 40° C. condition to provide 8.07 g of dried crystals. The obtained crystals contained 8.04 g (26.51 mmol) of γ-glutamyl-valyl-glycine crystals and 0.03 g (0.19 mmol) of valyl-glycine.

Example 7

Preparation of γ-Glutamyl-Valyl-Glycine Crystal

Pure water (28.7 mL) was added to 9.80 g (32.32 mmol) of γ-glutamyl-valyl-glycine and 1.68 g (9.63 mmol) of valyl-glycine, and these components were dissolved in pure water at 75° C. to provide a solution (mass ratio of valyl-glycine to γ-glutamyl-valyl-glycine in the solution=17 mass %). The obtained solution was subjected to crystal precipitation in the same manner as in Example 6 to obtain unwashed wet crystals. The obtained unwashed wet crystals were washed with 25 mL of 90% MeOH to provide 11.37 g of wet crystals. The wet crystals were dried under reduced pressure in a 40° C. condition to provide 7.65 g of dried crystals. The obtained crystals contained 7.61 g (25.08 mmol) of γ-glutamyl-valyl-glycine crystals and 0.04 g (0.24 mmol) of valyl-glycine.

Example 8

Preparation of γ-Glutamyl-Valyl-Glycine Crystal

Pure water (28.7 mL) was added to 10.00 g (32.97 mmol) of γ-glutamyl-valyl-glycine and 1.30 g (7.46 mmol) of valyl-glycine, and these components were dissolved in pure water at 75° C. to provide a solution (mass ratio of valyl-glycine to γ-glutamyl-valyl-glycine in the solution=13 mass %). The obtained solution was cooled to 50° C. at 10° C./hr. About 50 mg of seed crystals were added to the solution at 60° C. in the middle of the addition. The solution was kept at 50° C. for one hour after the temperature thereof reached 50° C., and 114.8 mL of MeOH was added to the solution over one hour. The solution was then cooled to 10° C. at 5° C./hr to precipitate crystals. After the solution containing the precipitated crystals was further kept at 10° C. for 10 hours or more, the precipitated crystals were separated to obtain 14.58 g of unwashed wet crystals. The wet crystals were dried under reduced pressure in a 40° C. condition to provide 8.07 g of dried crystals. The obtained crystals contained 7.89 g (26.00 mmol) of γ-glutamyl-valyl-glycine crystals and 0.17 g (0.96 mmol) of valyl-glycine.

Example 9

Preparation of γ-Glutamyl-Valyl-Glycine Crystal

Pure water (28.5 mL) was added to 9.95 g (32.80 mmol) of γ-glutamyl-valyl-glycine and 1.57 g (8.99 mmol) of valyl-glycine, and these components were dissolved in pure water at 75° C. to provide a solution (mass ratio of valyl-glycine to γ-glutamyl-valyl-glycine in the solution=16 mass %). The obtained solution was subjected to crystal precipitation in the same manner as in Example 8 to obtain unwashed wet crystals. The obtained unwashed wet crystals were washed with 10 mL of 90% MeOH to provide 15.2 g of wet crystals. The wet crystals were dried under reduced pressure in a 40° C. condition to provide 7.82 g of dried crystals. The obtained crystals contained 7.71 g (25.43 mmol) of γ-glutamyl-valyl-glycine crystals and 0.11 g (0.63 mmol) of valyl-glycine.

Comparative Example 2

Preparation of γ-Glutamyl-Valyl-Glycine Crystal

Pure water (28.5 mL) was added to 9.52 g (31.39 mmol) of γ-glutamyl-valyl-glycine and 1.97 g (11.28 mmol) of valyl-glycine, and these components were dissolved in pure water at 75° C. to provide a solution (mass ratio of valyl-glycine to γ-glutamyl-valyl-glycine in the solution=21 mass %). The obtained solution was subjected to crystal precipitation in the same manner as in Example 6 to obtain unwashed wet crystals. The obtained unwashed wet crystals were washed with 37 mL of 90% MeOH to provide 15.95 g of wet crystals. The wet crystals were dried under reduced pressure in a 40° C. condition to provide 8.16 g of dried crystals. The obtained crystals contained 7.23 g (23.84 mmol) of γ-glutamyl-valyl-glycine crystals and 0.93 g (5.35 mmol) of valyl-glycine.

Comparative Example 3

Preparation of γ-Glutamyl-Valyl-Glycine Crystal

Pure water (27.8 mL) was added to 9.80 g (32.32 mmol) of γ-glutamyl-valyl-glycine and 2.51 g (14.44 mmol) of valyl-glycine, and these components were dissolved in pure water at 75° C. to provide a solution (mass ratio of valyl-glycine to γ-glutamyl-valyl-glycine in the solution=26 mass %). The obtained solution was subjected to crystal precipitation in the same manner as in Example 6 to obtain unwashed wet crystals. The obtained unwashed wet crystals were washed with 40 mL of 90% MeOH to provide 18.72 g of wet crystals. The wet crystals were dried under reduced pressure in a 40° C. condition to provide 8.91 g of dried crystals. The obtained crystals contained 7.28 g (23.99 mmol) of γ-glutamyl-valyl-glycine crystals and 1.63 g (9.38 mmol) of valyl-glycine.

Comparative Example 4

Preparation of γ-Glutamyl-Valyl-Glycine Crystal

Pure water (28.1 mL) was added to 9.85 g (32.49 mmol) of γ-glutamyl-valyl-glycine and 2.05 g (11.76 mmol) of valyl-glycine, and these components were dissolved in pure water at 75° C. to provide a solution (mass ratio of valyl-glycine to γ-glutamyl-valyl-glycine in the solution=21 mass %). The obtained solution was subjected to crystal precipitation in the same manner as in Example 8 to obtain unwashed wet crystals. The obtained unwashed wet crystals were washed with 10 mL of 90% MeOH to provide 16.2 g of wet crystals. The wet crystals were dried under reduced pressure in a 40° C. condition to provide 8.24 g of dried crystals. The obtained crystals contained 7.57 g (24.97 mmol) of γ-glutamyl-valyl-glycine crystals and 0.67 g (3.84 mmol) of valyl-glycine.

Comparative Example 5

Preparation of γ-Glutamyl-Valyl-Glycine Crystal

Figure 5:
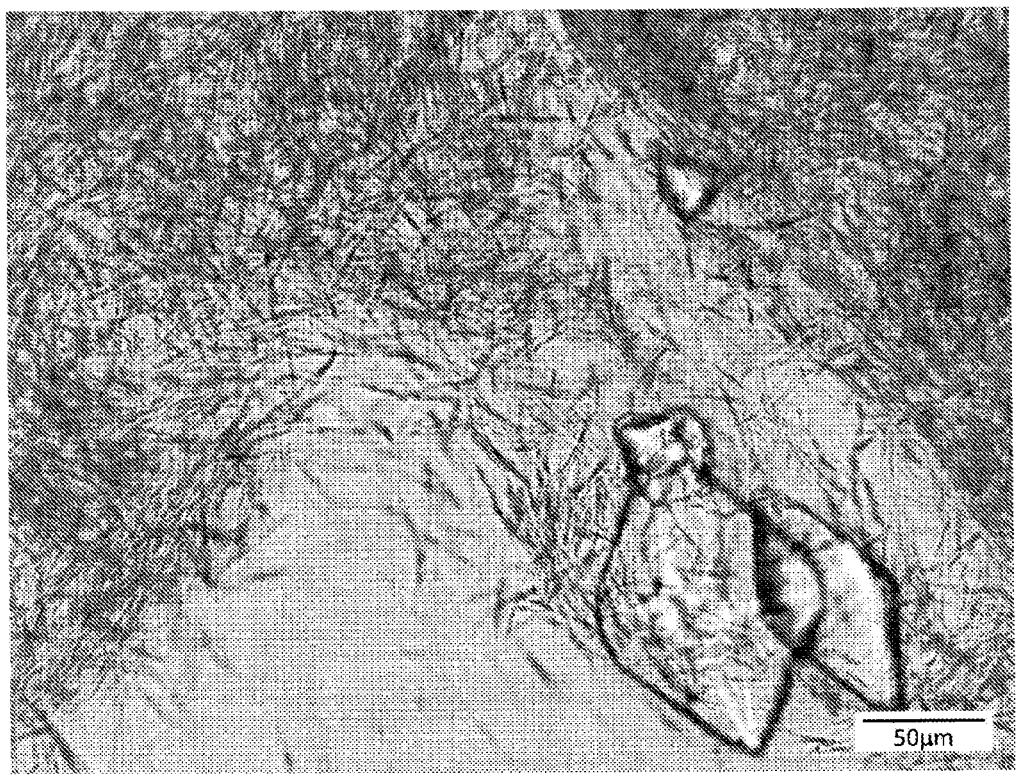
FIG. 5 shows an optical micrograph of γ-glutamyl-valyl-glycine crystals, obtained in Comparative Example 5.

A γ-glutamyl-valyl-glycine solution containing valyl-glycine obtained by the GGT enzyme reaction was heated at 80° C. for 30 minutes in an autoclave, and then cells contained in the solution were removed. The sterile solution (300.6 g) containing 8.80 g (29.01 mmol) of γ-glutamyl-valyl-glycine and 3.46 g (19.87 mmol) of valyl-glycine (mass ratio of valyl-glycine to γ-glutamyl-valyl-glycine in the solution=39 mass %) was concentrated to 76.04 g under reduced pressure and then 56 mL of MeOH was added to the solution over one hour while it was kept at 50° C. In the middle of the addition, 86.40 mg of seed crystals were added. The entire solution was then cooled to 10° C. at 5° C./hr to precipitate crystals. After the solution containing the precipitated crystals was further kept at 10° C. for 35 hours, the precipitated crystals were separated to obtain unwashed wet crystals. The obtained unwashed wet crystals were washed with 20 mL of 90 vol % MeOH to provide 14.72 g of wet crystals. The wet crystals were dried under vacuum in a 40° C. condition to provide 9.93 g of dried crystals. The obtained crystals (see the crystal photograph in FIG. 5) contained 3.09 g (10.19 mmol) of γ-glutamyl-valyl-glycine crystals, 0.004 g (0.013 mmol) of valyl-valyl-glycine, and 0.0002 g (0.001 mmol) of valyl-valine (crystallization yield: 35.1 mass %).

The results of Examples and Comparative Examples above are summarized in Tables 3-1 and 3-2 below.

TABLE 3-1

|  | Ex. 5 | Ex. 6 | Ex. 7 | Ex. 8 | Ex. 9 |
| --- | --- | --- | --- | --- | --- |
| VG/EVG in EVG solution (mass %) | 0.4 | 11 | 17 | 13 | 16 |
| MeOH conc. (vol %) in crystallization | 75 | 60 | 60 | 80 | 80 |
| Yield of EVG crystal (mass %) | 71.5 | 80.6 | 77.6 | 78.9 | 77.1 |
| Loss on drying (mass %) | 62.8 | 29.3 | 32.7 | 44.7 | 48.1 |
| Purity of EVG crystal (mass %) | 97.5 | 99.6 | 99.5 | 97.8 | 98.6 |
| Filtration rate (L/m² · h) | N.D. | 1150 | 860 | N.D. | N.D. |

TABLE 3-2

|  | Comp. Ex. 1 | Comp. Ex. 2 | Comp. Ex. 3 | Comp. Ex. 4 | Comp. Ex. 5 |
| --- | --- | --- | --- | --- | --- |
| VG/EVG in EVG solution (mass %) | 21 | 21 | 26 | 21 | 39 |
| MeOH conc. (vol %) in crystallization | 78 | 60 | 60 | 60 | 60 |
| Yield of EVG crystal (mass %) | 42.8 | 75.9 | 74.2 | 75.7 | 35.1 |
| Loss on drying (mass %) | N.D. | 48.8 | 52.4 | 49 | 32.5 |
| Purity of EVG crystal (mass %) | N.D. | 88.6 | 81.7 | 91.9 | 31.1 |

TABLE 3-2-continued

|  | Comp. Ex. 1 | Comp. Ex. 2 | Comp. Ex. 3 | Comp. Ex. 4 | Comp. Ex. 5 |
|---|---|---|---|---|---|
| Filter paper pore size (μm) | N.D. | 1 | 1 | N.D. | 3 |
| Filtration rate (L/m² · h) | N.D. | 80 | 60 | N.D. | 489 |

Tables 3-1 and 3-2 above indicated that the formation of the γ-glutamyl-valyl-glycine crystal after adjusting the amount of valyl-glycine or the salt thereof in the γ-glutamyl-valyl-glycine solution to 0.1 mass % or more and less than 20 mass % (Examples 5 to 9) increased the yield of the γ-glutamyl-valyl-glycine crystal as compared to Comparative Examples.

It was also indicated that the loss on drying was also decreased to provide excellent crystals in which the water content in the crystals before drying decreased. It was also indicated that large crystals having excellent filterability were obtained because of a significantly improved filtration rate. The loss on drying here is calculated according to the following equation.

Loss on drying (mass %)={(mass of crystal before drying−mass of crystal after drying)/mass of crystal before drying}×100

It was also indicated that crystals having an excellent purity were obtained. For the purity of the EVG crystals, the concentration of EVG ($X2$ g/ml) in an aqueous solution containing a predetermined amount of the crystal obtained in Examples or Comparative Examples ($X1$ g/ml) was determined with HPLC, and the purity of the crystal was obtained according to the following equation.

Purity (mass %)=$X1/X2$×100

As the column for the HPLC, Hydrosphere C18 produced by YMC Co., Ltd. (particle size: 5 μm, inner diameter: 4.6 mm, length: 250 mm) was used. As the eluent for the HPLC, solution A (50 mM potassium dihydrogen phosphate (pH 3.0, the pH was adjusted with phosphoric acid) and solution B (acetonitrile) were used. The column temperature was 30° C., and the UV detection wavelength was 210 nm. The gradient of the eluent was 0% solution B from 0 to 25 minutes, 0% to 40% solution B from 25 to 50 minutes, 40% to 0% solution B from 50 to 51 minutes, and 0% solution B from 51 to 70 minutes.

[2] Evaluation of γ-Glutamyl-Valyl-Glycine Crystals

The optical micrographs of the γ-glutamyl-valyl-glycine crystals obtained in Examples 6 and 7, and Comparative Examples 1 and 2 were shown in FIGS. 1 to 4, respectively. On the basis of these optical micrographs, the mean of the transverse diameter of the γ-glutamyl-valyl-glycine crystals in respective Examples shown in FIGS. 1 to 4 was determined.

Specifically, the crystals were photographed with an optical microscope. Ten crystals were randomly selected, and the transverse diameters thereof were determined to obtain the mean. The results are summarized in Table 4-1. The mean of the transverse diameter calculated using the above optical microscope, analysis software, and others is indicated in Table 4-2.

TABLE 4-1

|  | Ex. 6 | Ex. 7 | Comp. Ex. 2 | Comp. Ex. 3 |
|---|---|---|---|---|
| Valyl-glycine in γ-glutamyl-valyl-glycine solution (mass %) | 11 | 17 | 21 | 26 |
| Mean of transverse diameter (μm) | 3.75 | 2.91 | 2.31 | 1.32 |

TABLE 4-2

|  | Ex. 6 | Ex. 7 | Comp. Ex. 2 | Comp. Ex. 3 |
|---|---|---|---|---|
| Valyl-glycine in γ-glutamyl-valyl-glycine solution (mass %) | 11 | 17 | 21 | 26 |
| Mean of transverse diameter (μm) | 3.63 | 2.37 | 2.03 | 1.76 |

Tables 4-1 and 4-2 and FIGS. 1 to 4 indicates that the γ-glutamyl-valyl-glycine crystals obtained by the method of the present invention have a larger transverse diameter than Comparative Examples, that is, larger thicker γ-glutamyl-valyl-glycine crystals are obtained.

The content of valyl-valyl-glycine and valyl-valine in the crystals obtained in Example 5 and Comparative Example 1 was determined with the same HPLC conditions as described above. As a result, for the crystal of Example 5 formed with a crystallization yield of 71.5 mass %, 0.04 g (0.16 mmol) of valyl-valyl-glycine and 0.08 g (0.38 mmol) of valyl-valine were contained in 11.05 g of the dried crystal. For the crystal of Comparative Example 5 formed with a crystallization yield of 35.1 mass %, 0.004 g (0.013 mmol) of valyl-valyl-glycine and 0.0002 g (0.001 mmol) of valyl-valine were contained in 9.93 g of the dried crystal.

EXPLANATION OF SEQUENCE LISTING

SEQ ID NO: 1: Nucleotide sequence of *Escherichia coli* ggt gene
SEQ ID NO: 2: Amino acid sequence of *Escherichia coli* GGT
SEQ ID NO: 3: Nucleotide sequence of *Escherichia coli* pepD gene
SEQ ID NO: 4: Amino acid sequence of *Escherichia coli* PepD
SEQ ID NOS: 5 to 12: PCR primer for pSF12_ggt production
SEQ ID NOS: 13 to 14: PCR primer for pepD gene disruption

The invention claimed is:

1. A method for producing a γ-glutamyl-valyl-glycine crystal, comprising:
   reacting valyl-glycine or a salt thereof with a γ-glutamyl group donor in the presence of γ-glutamyl transferase or a γ-glutamyl transferase crude enzyme extract obtained from a microorganism expressing said transferase, to prepare a mixed solution of valyl-glycine or the salt thereof and γ-glutamyl-valyl-glycine, in which the mixed solution contains valyl-glycine in an amount of 20 mass % or more relative to the mass of γ-glutamyl-valyl-glycine;
   adjusting the amount of valyl-glycine or the salt thereof in the prepared mixed solution to 0.1 mass % or more and less than 20 mass % relative to the mass of γ-glutamyl-valyl-glycine in the solution to prepare a γ-glutamyl-valyl-glycine solution; and
   subjecting the γ-glutamyl-valyl-glycine solution to a crystallization procedure, comprising adding a poor solvent to the solution and then cooling the solution, to produce the γ-glutamyl-valyl-glycine crystal.

2. The method according to claim 1, wherein the amount of valyl-glycine or the salt thereof in the mixed solution is adjusted in a range of from 1 to 18 mass % relative to the mass of γ-glutamyl-valyl-glycine in the solution.

3. The method according to claim 1, wherein the amount of valyl-glycine or the salt thereof in the mixed solution is adjusted by adsorbing γ-glutamyl-valyl-glycine in the mixed solution to an adsorption resin and allowing valyl-glycine or the salt thereof in the mixed solution to flow through the adsorption resin, followed by elution of γ-glutamyl-valyl-glycine from the adsorption resin.

4. The method according to claim 1, wherein the γ-glutamyl group donator is glutamine.

5. The method according to claim 1, wherein γ-glutamyl transferase or the microorganism containing the enzyme is a bacterium belonging to the Enterobacteriaceae.

6. The method according to claim 5, wherein the bacterium is *Escherichia coli*.

7. The method according to claim 1, wherein valyl-glycine or the salt thereof is reacted with the γ-glutamyl group donator in a solvent selected from water and buffers.

8. The method according to claim 1, wherein the poor solvent comprises at least one member selected from the group consisting of an alcohol, an ether, an acetate ester, and a hydrocarbon.

9. The method according to claim 1, wherein the poor solvent comprises an alcohol.

10. The method according to claim 9, wherein the alcohol is methanol, ethanol or octanol.

11. The method according to claim 1, wherein after the poor solvent is added to the solution, the solution is cooled to a temperature within a range of 0 to 15° C.

12. The method according to claim 1, wherein after the poor solvent is added to the solution, the solution is cooled to a temperature within a range of 5 to 10° C.

* * * * *